US006929656B1

(12) United States Patent
Lennox

(10) Patent No.: US 6,929,656 B1
(45) Date of Patent: Aug. 16, 2005

(54) METHOD AND DEVICE FOR REDUCING SECONDARY BRAIN INJURY

(75) Inventor: Charles D. Lennox, Hudson, NH (US)

(73) Assignee: MedCool, Inc., Wellesley, MA (US)

( * ) Notice: Subject to any disclaimer, the term of this patent is extended or adjusted under 35 U.S.C. 154(b) by 6 days.

(21) Appl. No.: 10/243,583

(22) Filed: Sep. 13, 2002

Related U.S. Application Data

(60) Provisional application No. 60/322,391, filed on Sep. 14, 2001.

(51) Int. Cl.$^7$ .............................................. A61F 7/00
(52) U.S. Cl. ..................................... 607/105; 607/104
(58) Field of Search .......................... 607/96, 109, 110, 607/113, 114, 104, 105; 606/20–21

(56) References Cited

U.S. PATENT DOCUMENTS

| | | | |
|---|---|---|---|
| 5,342,301 A | 8/1994 | Saab | 604/96 |
| 5,486,208 A | 1/1996 | Ginsburg | 607/106 |
| 5,971,979 A | 10/1999 | Joye et al. | 606/21 |
| 6,217,552 B1 | 4/2001 | Barbut et al. | 604/113 |
| 6,623,514 B1 | 9/2003 | Chin | 607/105 |
| 6,648,878 B2 | 11/2003 | Lafontaine | 606/21 |
| 6,660,026 B2 * | 12/2003 | Larnard et al. | 607/104 |
| 6,682,508 B1 | 1/2004 | Meythaler et al. | 604/246 |
| 6,692,519 B1 | 2/2004 | Hayes, Jr. | 607/105 |
| 6,699,269 B2 | 3/2004 | Khanna | 607/105 |
| 2002/0198579 A1 * | 12/2002 | Khanna | 607/105 |

OTHER PUBLICATIONS

Piepgras, et al., "Rapid Active Internal Core Cooling for Induction of Moderate Hypothermia in Head Injury by Use of an Extracorporeal Heat Exchanger", Neurosurgery Online, Feb. 1998, vol. 42, No. 2. http://www.neurosurgery-online.com. Visited Nov. 24, 2003.

Alsius, A New Degree of Care, The Fortius Catheter, http://www.alsius.com/us/fortius.htm. Visited Nov. 24, 2003.

Hachimi-Idrissi, et al., "Mild Hypothermia Induced by a Helmet Device: A Clinical Feasibility Study", Resuscitation 51:275 (2001).

Ommaya, et al., "Direct Extravascular Brain Cooling in the Normothermic Animal", Neurology 12:882 (1962).

Tooley, et al., "Significant Selective Head Cooling can be Maintained Long-Term After Global Hypoxia Ischemia in Newborn Piglets", Pediatrics, vol. 109, No. 4, pp. 643-649, Apr. 2002.

(Continued)

*Primary Examiner*—Roy D. Gibson
(74) *Attorney, Agent, or Firm*—Thomas J. Engellenner; Jeffrey J. Duquette; Nutter McClennen & Fish LLP

(57) ABSTRACT

Disclosed is an apparatus and method for reducing secondary brain injury. The apparatus includes a brain-cooling probe and a control console. The brain-cooling probe cools the brain to prevent secondary injury by cooling the cerebrospinal fluid within one or more brain ventricles. The brain-cooling probe withdraws a small amount of cerebrospinal fluid from a ventricle into a cooling chamber located ex-vivo in close proximity to the head. After the cerebrospinal fluid is cooled it is then reintroduced back into the ventricle. This process is repeated in a cyclical or continuous manner in order to achieve and maintain a predetermined brain ventricle temperature lower than normal body temperature. The apparatus and method disclosed provides effective brain ventricle cooling without the need to introduce extra-corporeal fluids into the brain.

43 Claims, 19 Drawing Sheets

OTHER PUBLICATIONS

Javid, et al., "Hypothermic Ventricular Perfusion: Evaluation of Use in Cerebrovascular Occlusion New York, State Journal of Medicine", pp. 248-251, Jan. 5, 1967.

Tooley, et al., "Head Cooling with Mild Systemic Hypothermia in Anesthetized Piglets is Neuroprotective", Annals of Neurology, vol. 53, No. 1, pp. 65-72, Jan. 2002.

White, M.D., "Cerebral Hypothermia and Circulatory Arrest: Review and Commentary", Mayo Clin. Proc. 53:450 (1978).

Costal, et al., "Experimental Production of Cerebral Hypothermia by Ventricular Perfusion Techniques", J. Neurosurg, 20:112 (1963).

* cited by examiner

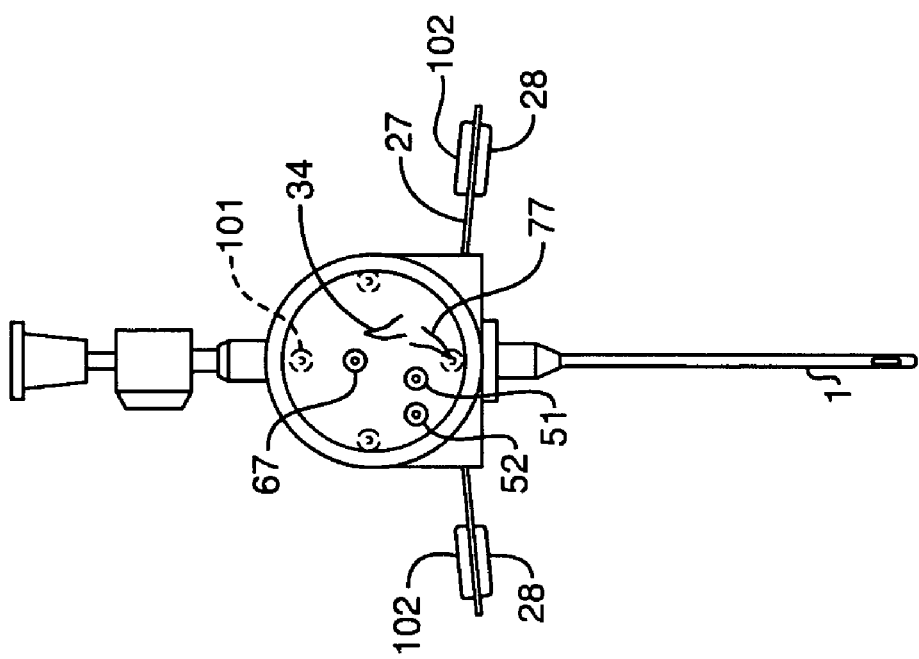
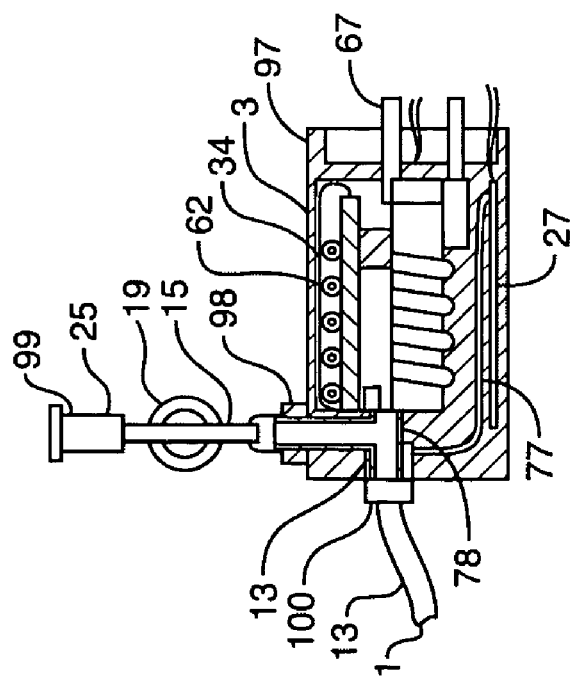
FIG. 10B
FIG. 10A

METHOD AND DEVICE FOR REDUCING SECONDARY BRAIN INJURY

CROSS REFERENCE TO RELATED APPLICATIONS

This application is entitled to the benefit of Provisional Patent Application Ser. Nr. 60/322,391 filed 2001 Sep. 14.

BACKGROUND

1. Field of Invention

This invention relates to a method and device for inducing global cerebral hypothermia for the prevention of secondary brain injury from stroke, trauma, or surgery.

2. Description of Prior Art

Patients suffering from stroke or head trauma, or have undergone invasive brain surgery are at risk from secondary brain injury. Secondary brain injury is a result of the innate healing response of the brain to the original insult caused by several not completely understood mechanisms. Regardless of the specific mechanisms involved, the end result is swelling of the brain caused by edema, which can lead to a critical or terminal rise in intra-cranial pressure.

It has long been known that hypothermia is neuroprotective. Hypothermia has a positive affect on all know mechanisms that lead to secondary brain injury. Hypothermia is routinely used during brain and other invasive surgeries to protect the brain from surgical interruptions in blood flow. Hypothermia has also been shown to be effective in controlling swelling of the brain in trauma and stroke patients.

The effectiveness of hypothermia is a function of depth and duration; the deeper the hypothermia, and/or the longer it is applied the more neuroprotective it is. However, hypothermia has historically been applied systemically, and the depth and duration of hypothermia is limited by the patient's ability to tolerate the therapy.

Systemic hypothermia has historically been accomplished by immersion of the patient's body in a cool bath. Today there are several commercial systemic hypothermia systems available. They consist of blankets or pads where cooled water is circulated through channels in the walls of the blanket or pad, and the patient's body is maintained in intimate contact. Medivan Corp. manufactures an example of a modern hypothermia system under the trade name Arctic Sun Cooling System.

Systemic hypothermia has been demonstrated to be effective in reducing secondary injury from stroke, trauma, and surgery however, there are several drawbacks to this approach: 1) It takes several hours to lower a patient's body to therapeutic temperatures. This delay in achieving therapeutic temperatures allows for the progression of irreversible secondary injury to the brain. 2) The practical therapeutic hypothermic temperature and duration is limited by the ability of the patient to tolerate, or survive the therapy. 3) The side effects of systemic hypothermia are frequent and can be life threatening, especially in frail patients. Side effects include shivering, cardiac arrhythmia and arrest, pneumonia, infections, and coagulation disorders. 4) The target of hypothermia therapy is the brain; therefore inducing hypothermia systemically places the patient at undue risk. 5) During the "critical phase" (rewarming period) of hypothermia treatment, there is no effective way to manage a sudden and critical increase in intra-cranial pressure, since re-cooling the body to reverse the increase in intra-cranial pressure takes several hours. 6) Systemic hypothermia poses significant clinical and logistical patient management issues.

There are several examples in the art where catheters are constructed with a cooling means, which is placed into the carotid artery to cool the blood entering the head. This offers an advantage over systemic hypothermia, since it provides a means to cool the head to lower temperatures than the rest of the body, but it still results in systemic hypothermia. Also, since the scientific evidence suggests that hypothermia must be maintained for extended periods of time, there is a great risk that clots will form on the catheters and migrate into the brain leading to episodes of stroke.

Nowhere in the art is it suggested that cooling the cerebrospinal fluid in a ventricle of the brain may induce global cerebral hypothermia and therefore prevent secondary brain injury. Nowhere in the art is it suggested that cerebral hypothermia can be accomplished by removing a portion of the cerebrospinal fluid from a brain ventricle, then cooling the removed cerebrospinal fluid ex vivo, then reintroducing the cooled cerebrospinal fluid back into the brain ventricle in a continuous or cyclical manner.

SUMMARY

Therefore, it is an object of this invention to provide a method and apparatus for preventing secondary brain injury.

In accordance with one aspect of this invention, secondary brain injury is prevented by placement of the distal end of a probe in to a ventricle of the brain and then, in a continuous or cyclical manner, using said probe to remove a portion of the cerebrospinal fluid contained in said ventricle into a cooling chamber located ex vivo at the proximal end of said probe, then cooling said cerebrospinal fluid in the cooling chamber of said probe, then reintroducing said cooled cerebrospinal fluid back into said ventricle, thereby cooling the brain while otherwise maintaining normal temperature in the rest of the body. In accordance with another aspect of this invention, secondary injury is prevented by placement of the distal end of a probe into a ventricle of the brain, and then using said probe to cool the cerebrospinal fluid within said ventricle to a predetermined temperature for a predetermined time where said probe functions in a continuous or cyclical manner to remove a portion of the cerebrospinal fluid contained in said ventricle into a cooling chamber located ex vivo at the proximal end of said probe, then cooling said cerebrospinal fluid in the cooling chamber of said probe, then reintroducing said cooled cerebrospinal fluid back into said ventricle, thereby cooling the brain while otherwise maintaining normal temperature in the rest of the body. In accordance with another aspect of this invention, secondary brain injury is prevented by placement of the distal end of a probe into a ventricle of the brain, and then using said probe to cool the cerebrospinal fluid contained within said ventricle to a predetermined temperature, where then the temperature is increased gradually over a period of time from the initial low temperature, to normal body temperature, with the period of time being greater than one hour and less than two months, where said probe functions in a continuous or cyclical manner to remove a portion of said cerebrospinal fluid contained in said ventricle into a cooling chamber located ex vivo at the proximal end of said probe, then cooling said cerebrospinal fluid in said cooling chamber of said probe, then reintroducing said cooled cerebrospinal fluid back into said ventricle, thereby cooling the brain while otherwise maintaining normal temperature in the rest of the body. In accordance with another aspect of this invention, secondary brain injury is prevented by placement of the distal end of a probe into a ventricle of the brain, and then using said probe to cool the cerebrospinal fluid within the ventricle to a degree based on the physiological response to said cooling, where said probe functions in a continuous or cyclical manner to remove a portion of the cerebrospinal fluid contained within said ventricle into a cooling chamber located ex vivo at the proximal end of said probe, then cooling said cerebrospinal fluid in said cooling chamber of the probe, then reintroducing said cooled cerebrospinal fluid back into said ventricle, thereby cooling the brain while otherwise maintaining normal temperature in the rest of the body. In accordance with another aspect of this invention, apparatus for preventing secondary brain injury includes a probe, an introducer sheath, a stereotaxic ventricle access needle, and a control console where the introducer sheath and stereotaxic ventricle access needle are constructed to integrally provide access to a ventricle of the brain by standard stereotaxic neurosurgical means, and where the distal end of said probe is placed into said ventricle through said introducer sheath, and where said probe functions in a continuous or cyclical manner to remove a portion of the cerebrospinal fluid contained within said ventricle into a cooling chamber located ex vivo at the proximal end of said probe, then cooling said cerebrospinal fluid in said cooling chamber of said probe, then reintroducing said cooled cerebrospinal fluid back into said ventricle, thereby cooling the brain while otherwise maintaining normal temperature in the rest of the body, and where the control console provides said probe with a means to remove cerebrospinal fluid from a ventricle of the brain, a means to cool cerebrospinal fluid, a means to reintroduce cerebrospinal fluid back into said ventricle, and a means to control said process of removing, cooling, and reintroducing cerebrospinal fluid. In accordance with another aspect of this invention, apparatus for preventing secondary brain injury includes a probe as described above where the distal end of the probe contains a mechanism near the distal tip of said probe to sense the temperature of cerebrospinal fluid contained in a ventricle of the brain. In accordance with another aspect of this invention, apparatus for preventing secondary brain injury includes a probe as described above where the distal end of the probe contains a mechanism near the distal tip of said probe to sense the pressure of cerebrospinal fluid contained in a ventricle of the brain. In accordance with another aspect of this invention, apparatus for preventing secondary brain injury includes a probe as described above where said probe provides for a means to drain excess cerebrospinal fluid from the ventricle of the brain. In another aspect of this invention, apparatus for preventing secondary brain injury includes a probe as described above, and an introducer sheath as described above, where said probe and said introducer sheath are constructed to integrally provide for an extended period of cooling and indwelling in a ventricle of the brain, with the period of cooling and indwelling being greater than one hour, and as long as two months.

OBJECTS AND ADVANTAGES

Accordingly, besides the objects and advantages of the method and apparatus to prevent secondary brain injury described in my patent above, several objects and advantages of the present invention are:

(a) to provide global cerebral hypothermia to a brain at risk of secondary injury to the degree that offers maximum clinical benefit without inducing hypothermia in the rest of the body;

(b) to provide global cerebral hypothermia to a brain at risk of secondary injury where the method for inducing hypothermia takes advantage of the fact that the cerebrospinal fluid in a ventricle of the brain can be cooled by a small caliber probe, and brain tissue surrounding the ventricle may be cooled by heat conduction into the ventricle to the extent that prevents secondary injury.

(c) to provide global cerebral hypothermia to a brain at risk of secondary injury within a minimal time after patient presentation where therapeutic temperatures are achieved rapidly due to the fact that only the brain is cooled;

(d) to provide global cerebral hypothermia to a brain at risk of secondary injury where the degree of hypothermia is adjusted according to the physiological response to hypothermia, where the physiological response to hypothermia is a change in intra-cranial pressure;

(e) to provide global cerebral hypothermia to a brain at risk of secondary injury where the degree of hypothermia is adjusted according to the physiological response to hypothermia, where the physiological response to hypothermia is a change in patient symptoms.

(f) to provide global cerebral hypothermia to a brain at risk of secondary injury where the degree of hypothermia is adjusted according to the physiological response to hypothermia, where the physiological response to hypothermia is a change in localized blood perfusion;

(g) to provide global cerebral hypothermia to a brain at risk of secondary injury where the degree of hypothermia is adjusted according to the physiological response to hypothermia, where the physiological response to hypothermia is a change in the size of the volume of infarcted tissue;

(h) to provide global cerebral hypothermia to a brain at risk of secondary injury where the degree of hypothermia is adjusted according to the physiological response to hypothermia, where the physiological response to hypothermia is a change in blood chemistry.

(i) to provide apparatus for inducing global cerebral hypothermia to a brain tissue at risk of secondary injury according to the objectives stated above;

(j) to provide a brain cooling probe system that consists of a brain cooling probe, an introducer sheath, a stereotaxic ventricle access needle, and a control console;

(k) to provide a brain cooling probe system that is constructed to cool the cerebrospinal fluid contained within a ventricle of the brain where said cooling means is ex vivo;

(l) to provide a brain cooling probe system that is constructed to be placed into a ventricle of the brain by stereotaxic radiological guidance using well known surgical methods;

(m) to provide a brain cooling probe system that is constructed to provide for long term cooling and indwelling;

(n) to provide a brain cooling probe system that is constructed to provide for fixation to the head of the patient;

(o) to provide a brain cooling probe system that is constructed to provide for protection against infection;

(p) to provide a brain cooling probe system that is constructed to provide for a means to sense a response to cooling;

(q) to provide a brain cooling probe system that is constructed to provide for a means to control the degree of cooling applied to the surrounding brain tissue.

DRAWING FIGURES

FIG. 1 shows a sagittal section of a human head with the brain probe, cooling assembly and introducer sheath fixated to the head with the distal end of the probe and the introducer sheath placed into a ventricle of the brain.

FIG. 2A. shows a side view of the brain probe and cooling assembly. FIG. 2B shows an end view of the brain probe and cooling probe FIG. 3 shows the introducer sheath.

FIG. 10A shows a sectional view of the construction of the cooling assembly. FIG. 10B and end view of the cooling assembly.

Figure 11A:
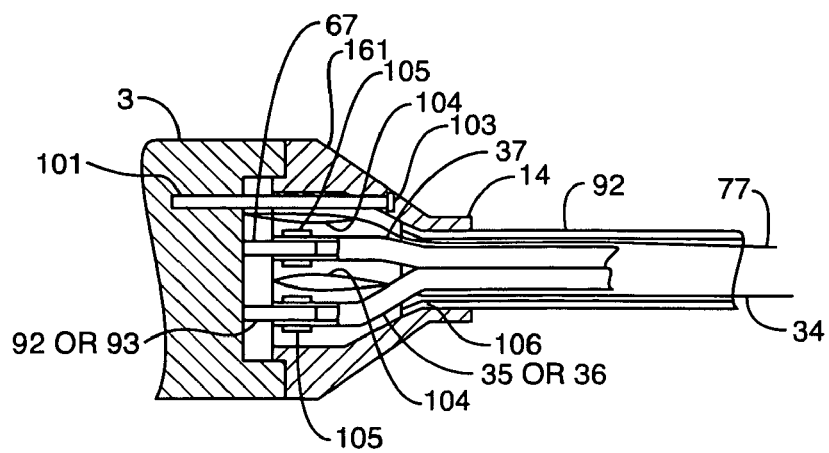
Figure 11G:
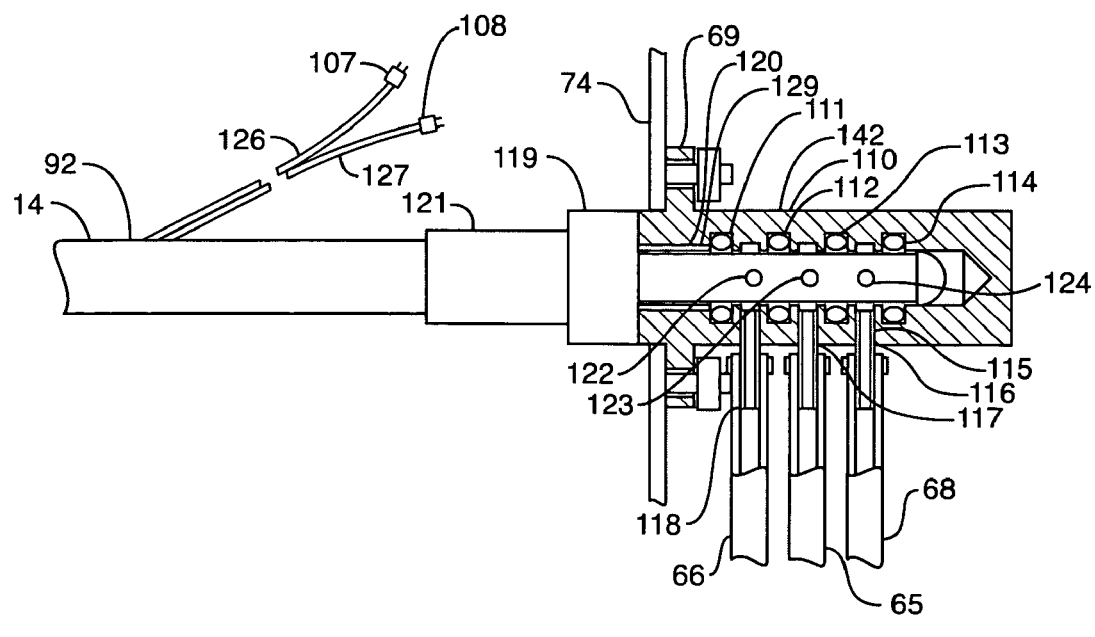
Figure 11B:
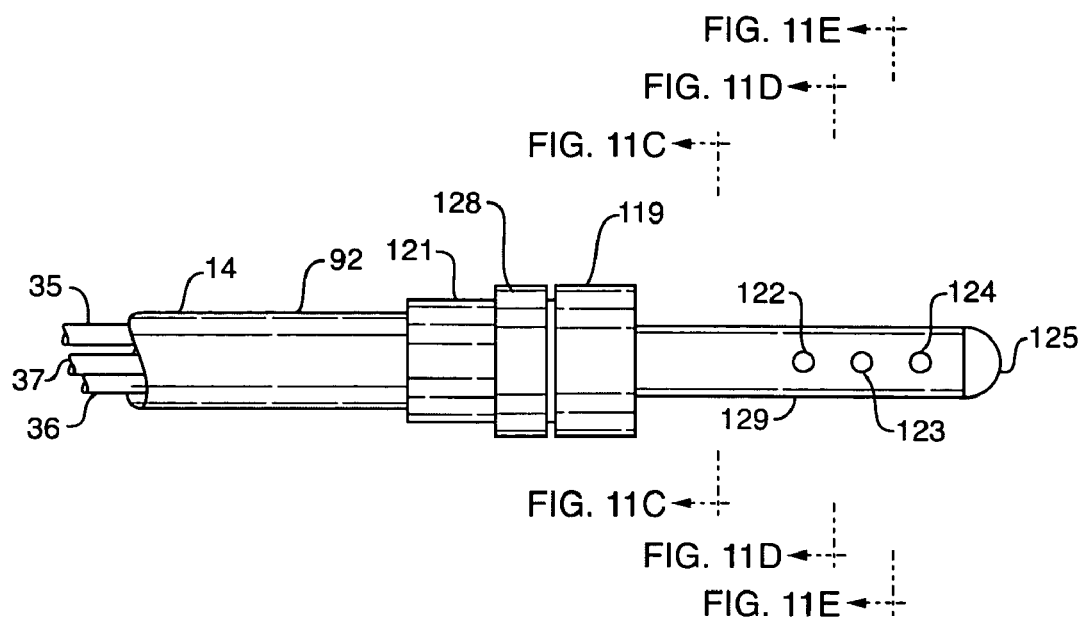

FIG. 11A shows a sectional view of the umbilical attachment to the cooling assembly. FIG. 11B shows the console plug assembly of the umbilical assembly. FIGS. 11C–11F show a sectional views of the console plug assembly. FIG. 11G shows the interaction between the console plug assembly, and the console receptacle.

Figure 12A:
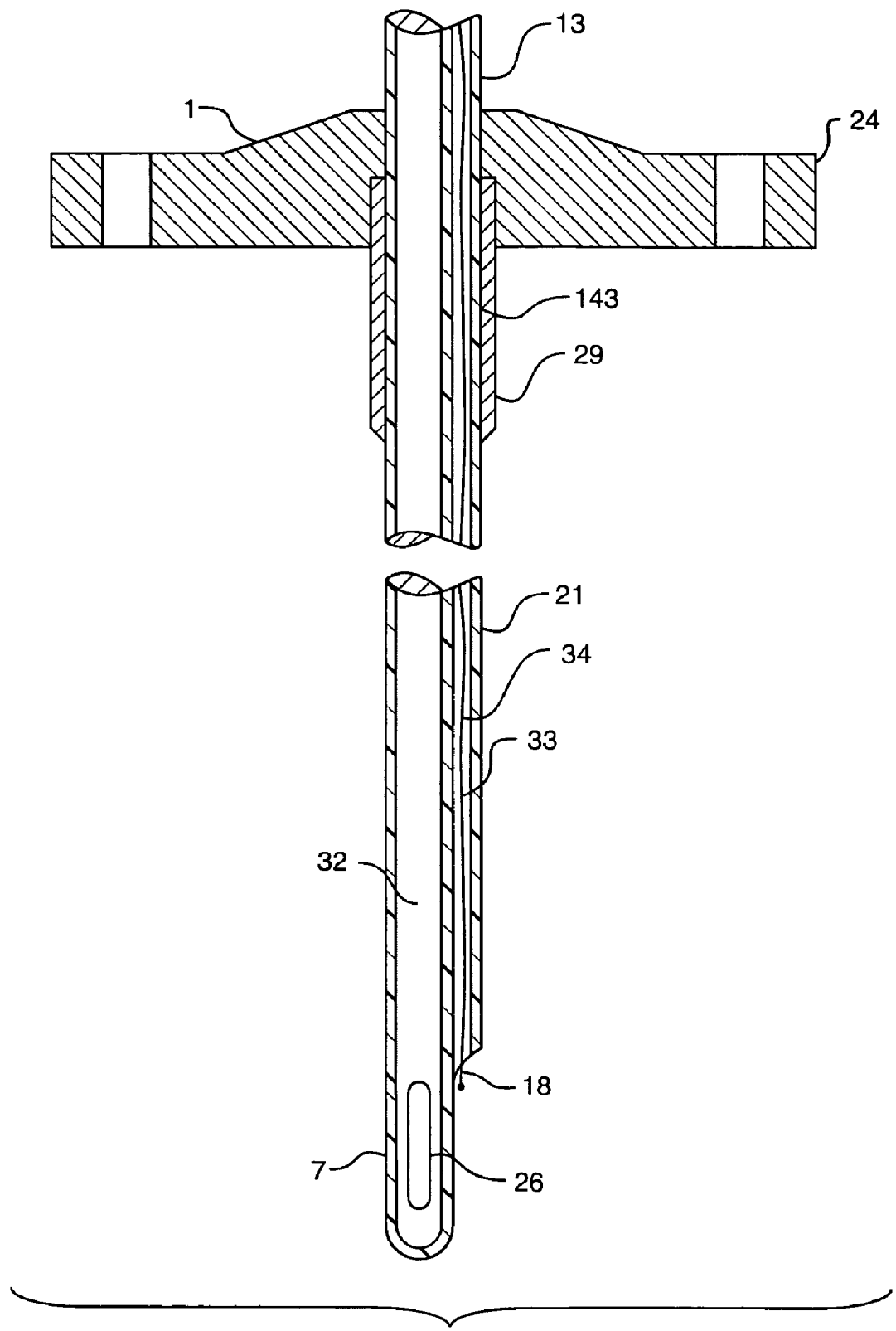
Figure 12B:
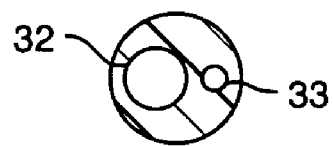

FIG. 12A shows a sectional view of the brain probe. FIG. 12B shows a sectional view of the brain probe shaft.

Figure 13:
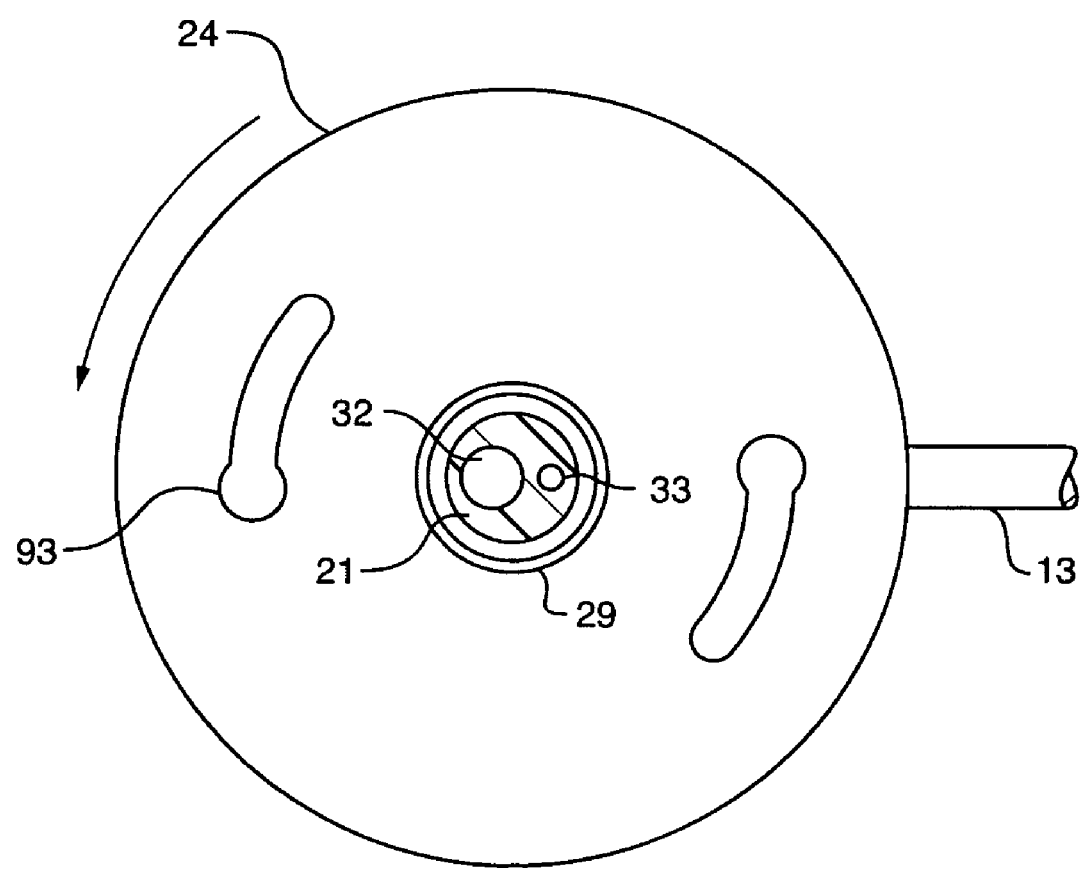

FIG. 13 shows a bottom view of the brain probe depicting the brain probe/introducer sheath docking mechanism.

Figure 14:
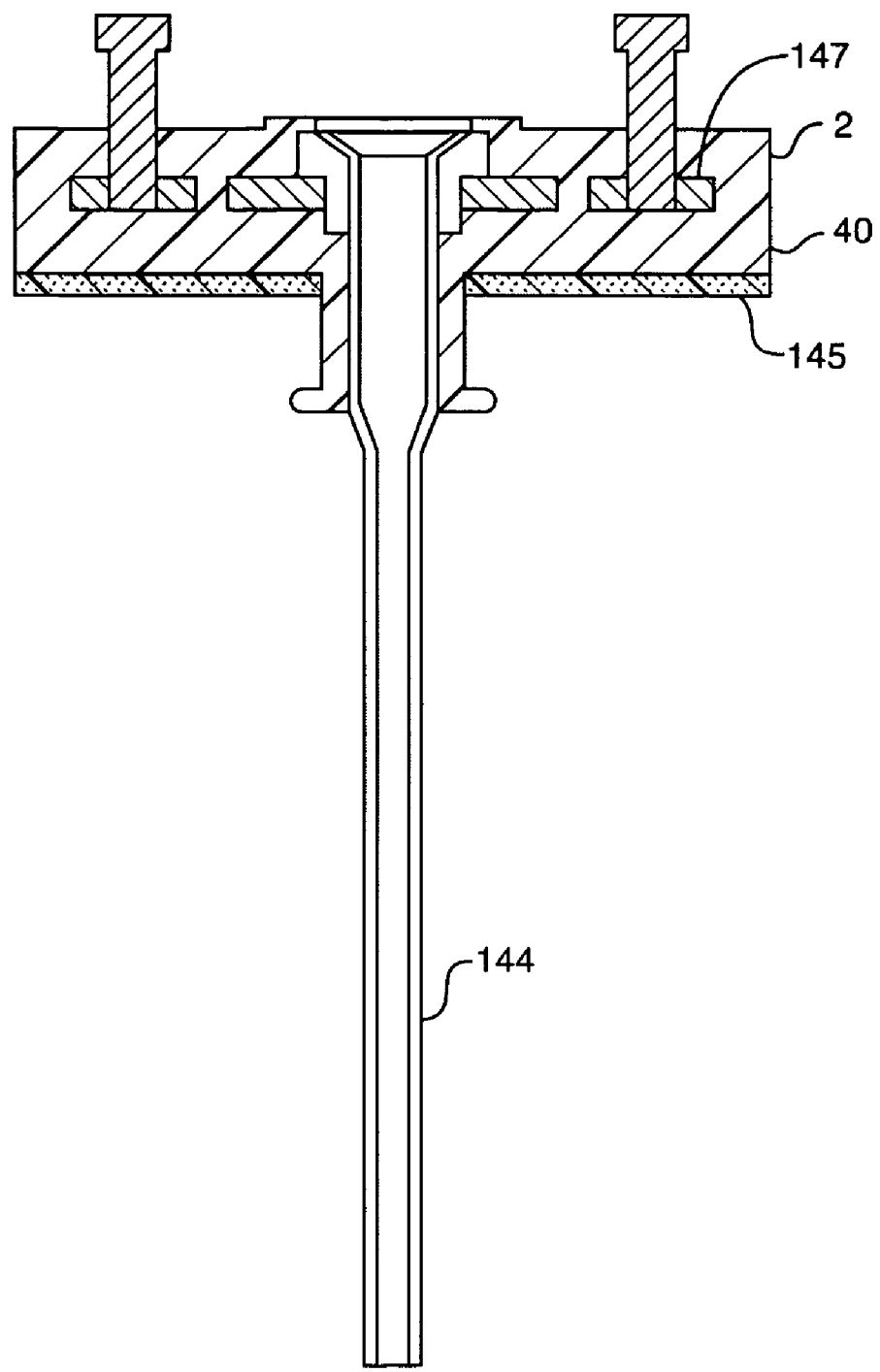

FIG. 14 shows a sectional view of the introducer sheath.

Figure 15B:
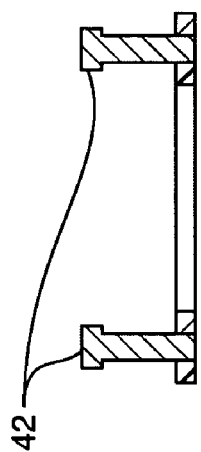
Figure 15A:
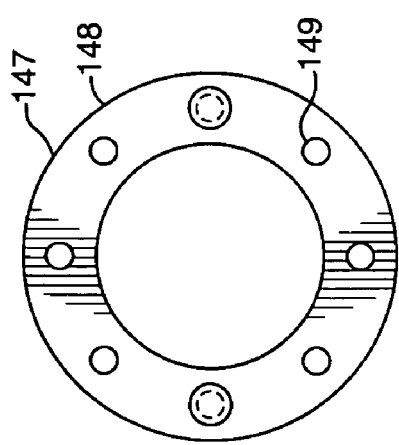

FIG. 15A shows a view of the construction of the docking ring assembly. FIG. 15B shows a sectional view of the docking ring assembly.

Figure 16:
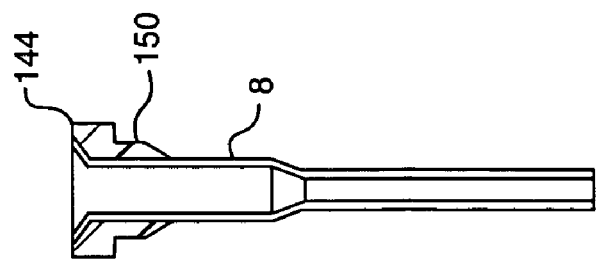

FIG. 16 shows a sectional view of the introducer sheath tube assembly.

Figure 17A:
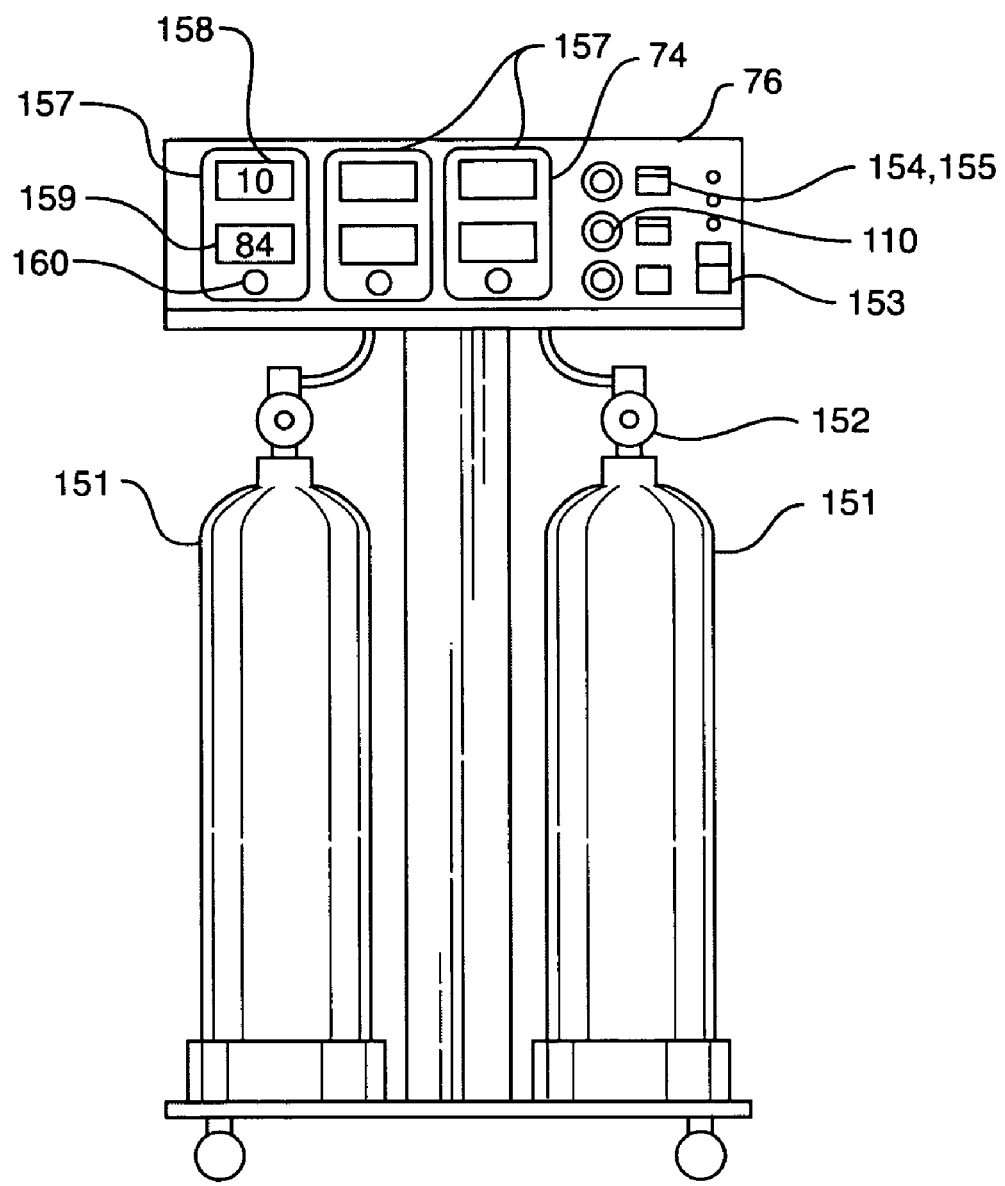
Figure 17B:
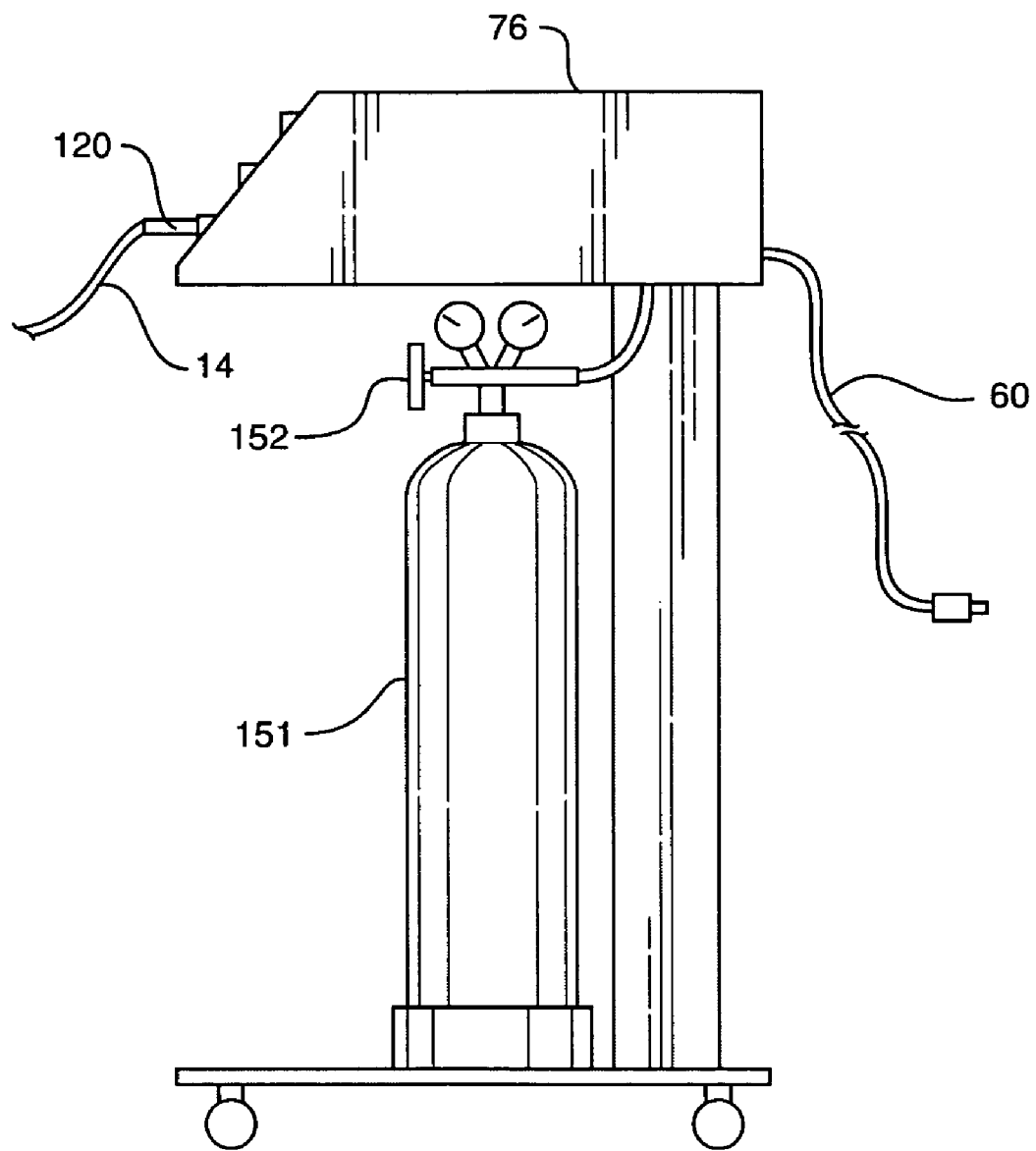

FIG. 17A shows a front view of the control console. FIG. 17B shows a side view of the control console.

Figure 18:
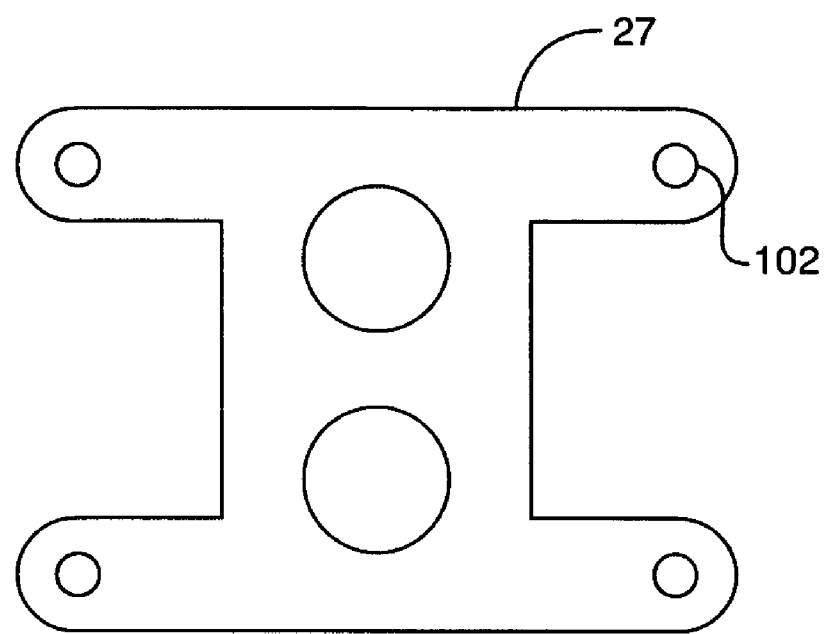

FIG. 18 shows a view of the cooling assembly mounting plate.

DESCRIPTION—FIGS. 1–6 PREFERRED OPERATIONAL EMBODIMENTS

Figure 1:
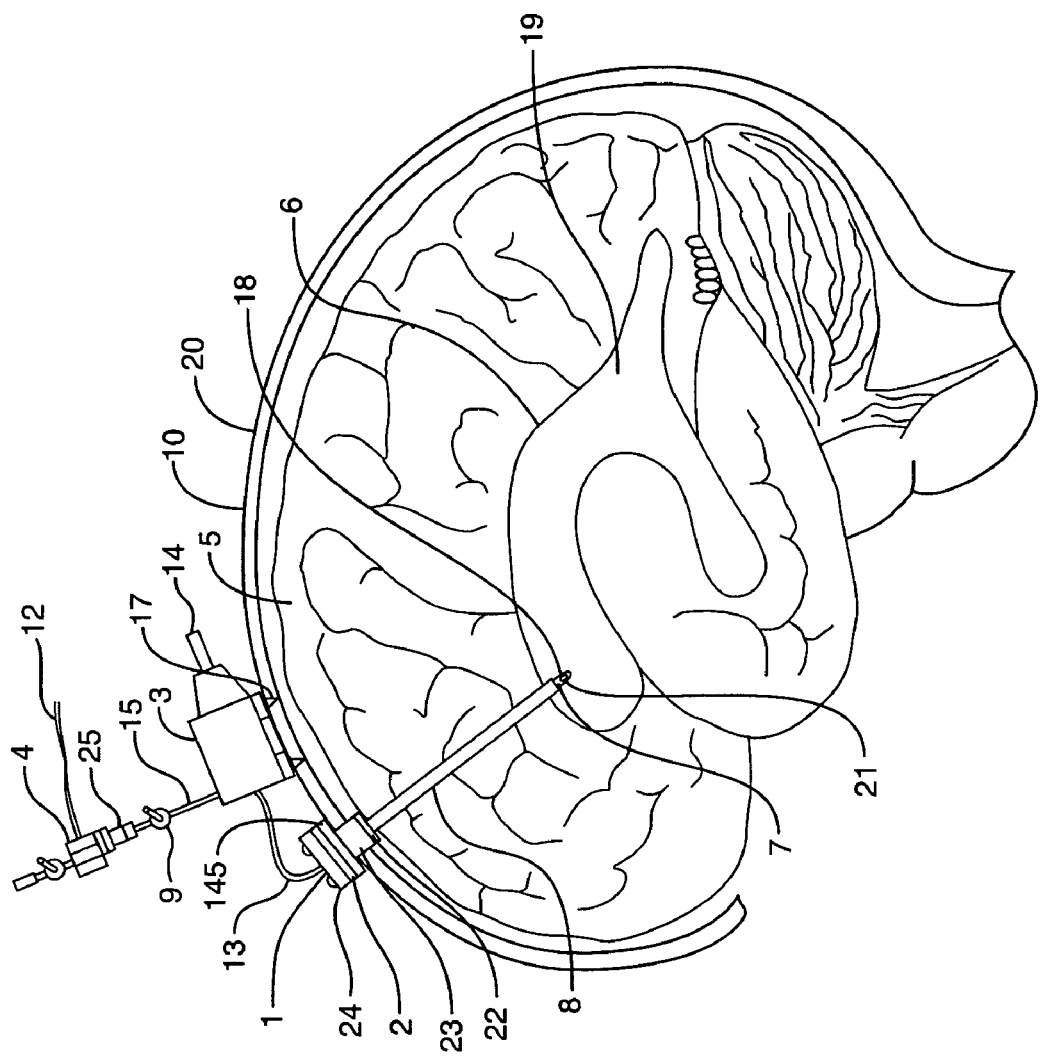

FIG. 1 depicts, in simplified form, a section of the head 20 with a brain probe 1 and introducer sheath 2 in operational position and cooling assembly 3 mounted on the head 20 with self-tapping bone screws 17. The distal end 7 of probe 1, and the distal end of introducer sheath 2 is located in a lateral ventricle of the brain 6. Probe tube 13 connects probe 1 to cooling assembly 3 and provides fluid communication from the probe 1 to cooling assembly 3. The distal end 7 of probe 1 contains a thermocouple 18 (FIG. 2B), which measures the temperature of the cerebrospinal fluid 19 contained in ventricle 6. The shaft 21 of probe 1 passes through the introducer sheath 2 introducer sheath tube 8 and connects the distal end 7 of probe 1 to the sheath docking collar 24 of probe 1 (See FIG. 8). Probe shaft 21 provides fluid communication from the ventricle 6 to probe tube 13 which therefore provides fluid communication from ventricle 6 to cooling assembly 3. The probe and introducer sheath 1&2 is fixated to the head 20 by outward expansion of the fixation plug 22 of introducer sheath 2 against the surgically created craniotomy hole 23 in the skull 10. The fixating plug as 22 seals the craniotomy hole 23 and prevents infection, providing for long term indwelling (greater than 1 hour and as long as two months) of the probe and introducer sheath 1&2 in the brain 5. Antiseptic pad 145 provides further protection against infection. Fluid tube 15, stop cock 9, and luer fitting 25 provides fluid communication from the ventricle 6 via probe shaft 21 of probe 1, and cooling assembly 3 and provides for drainage of excess cerebrospinal fluid from the ventricle. A commercially available physiological pressure sensor 4 may be mounted to luer fitting 25 to monitor cerebrospinal fluid pressure. Electrical cable 12 connects the pressure sensor 4 to the pressure meter (not shown). The cooling assembly 3 is connected to control console 76 by umbilical 14. During operation a portion of cerebrospinal fluid 19 (1 cc to 20 cc) is drawn from ventricle 6 into cooling assembly 3 through probe 1 and probe tube 13. The cerebrospinal fluid drawn into cooling assembly 3 is then cooled to between 0 Deg. C. and 25 Deg. C. The cooled cerebrospinal fluid 19 is then reintroduced into the ventricle 6 via probe tube 13 and probe 1. This cycle is repeated as necessary until the temperature within the ventricle 6 is between 10 Deg. C. and 36 Deg. C. as measured by thermocouple 18.

Figure 2B:
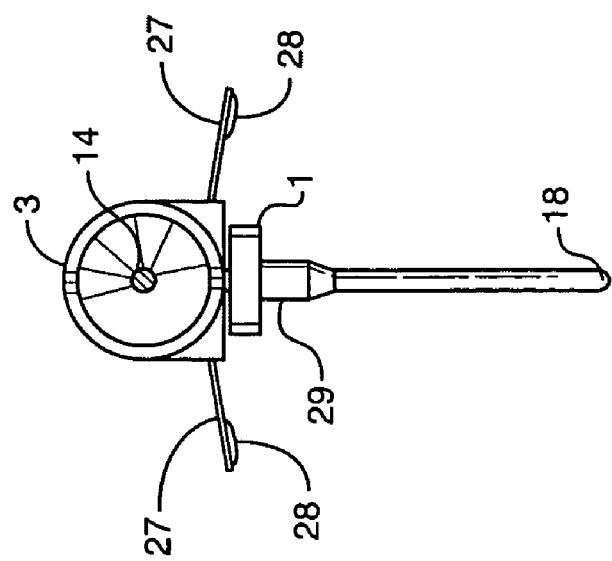
Figure 2A:
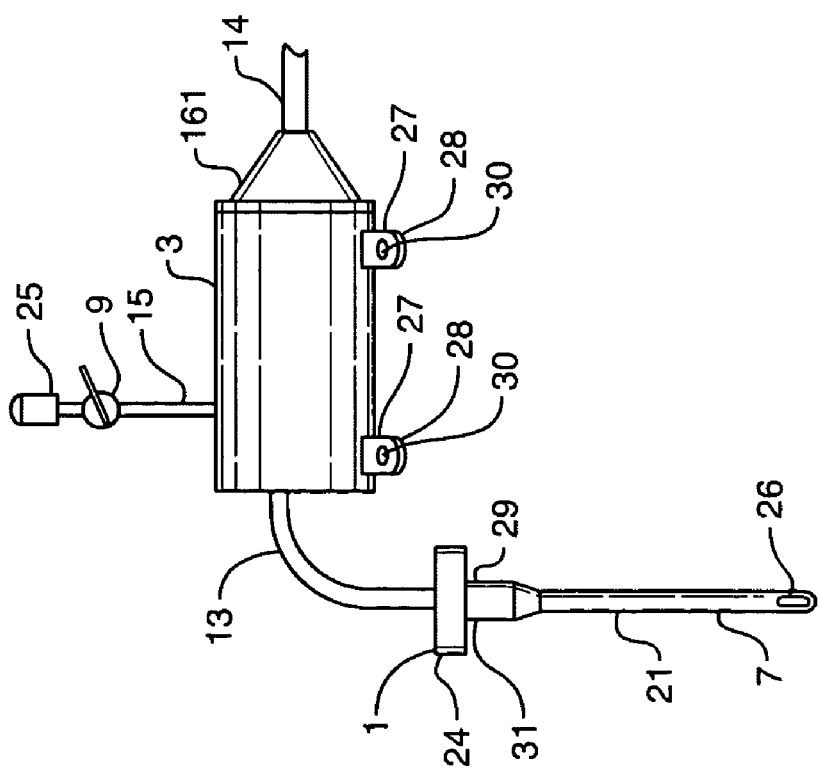
Figure 6:
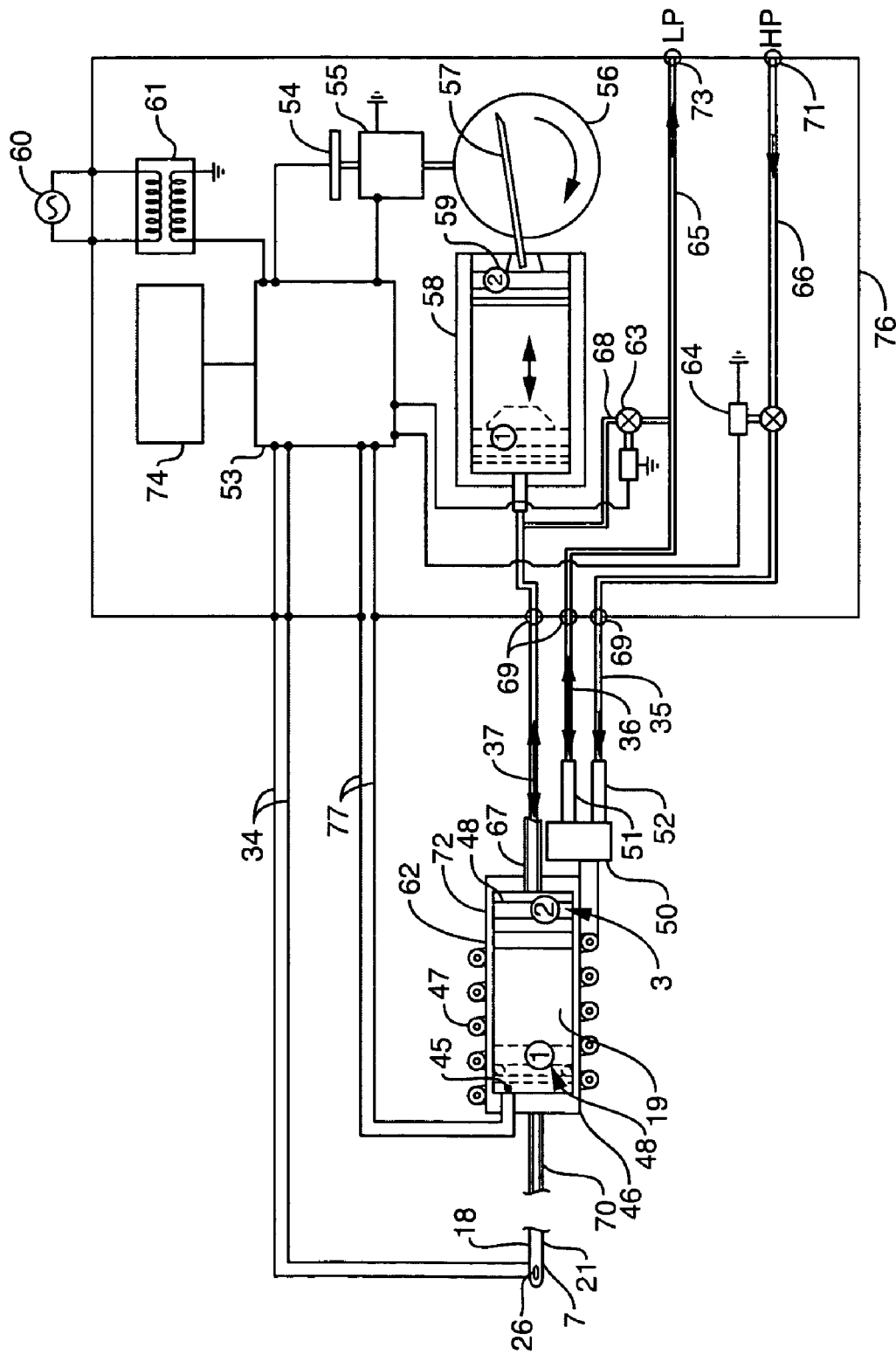
FIG. 6 shows in schematic form the preferred embodiment of the integral operation of the brain probe, cooling assembly and the control console.

FIG. 2A depicts a side view of brain probe 1 and cooling assembly 3. FIG. 2B depicts an end view of brain probe 1 and cooling assembly 3. Probe tube 13 connects probe 1 to cooling assembly 3 and provides fluid communication from distal tip 7 of probe 1 to cooling assembly 3. Fluid tube 13 also contains thermocouple wires that connect thermocouple 18 mounted on distal tip 7 of probe 1 to control console 76 via umbilical 14. Fluid tube 15, stop cock 9 and luer fitting 25 provides for drainage of excess cerebrospinal fluid 19. Probe 1 consists of probe shaft 21, sheath expansion plug 29, sheath docking collar 24, and thermocouple 18. Fluid port 26 at distal end 7 of probe shaft 21 provides fluid communication from ventricle 6 (FIG. 1) into shaft 21. Thermocouple 18 at distal end 7 of probe shaft 21 senses temperature of cerebrospinal fluid 19 in ventricle 6 (FIG. 1). Signals from thermocouple 18 are sent to control console 76 and are used to control brain cooling. Probe shaft 21 connects distal end 7 of probe 1 to proximal end 31 of probe 1 and provides fluid communication from distal end 7 to proximal end 31. Probe shaft 21 contains a fluid communication lumen 32, and thermocouple lead lumen 33 (FIGS. 12A & B). Sheath expansion plug 29 and sheath docking collar 24 work integrally with introducer sheath 2 to fixate the probe 1 and introducer sheath 2 to the head 20 and to seal the craniotomy hole 23 to prevent infection. Cooling assembly 3 is mounted to head 20 (FIG. 1) with (4) mounting tabs 27, and self-tapping screws 17 (FIG. 1). Rubber feet 28 provides for hermetic sealing of screw 17 to prevent infection. Umbilical 14 connects cooling assembly 3 to control console 76 and contains gas lines 35 & 36 for cooling, pneumatic line 37 for actuating cerebrospinal fluid removal and replacement, and thermocouple leads 34 & 77 (FIG. 6). Umbilical retaining flange 161 secures umbilical 14 to cooling assembly 3.

Figure 3:
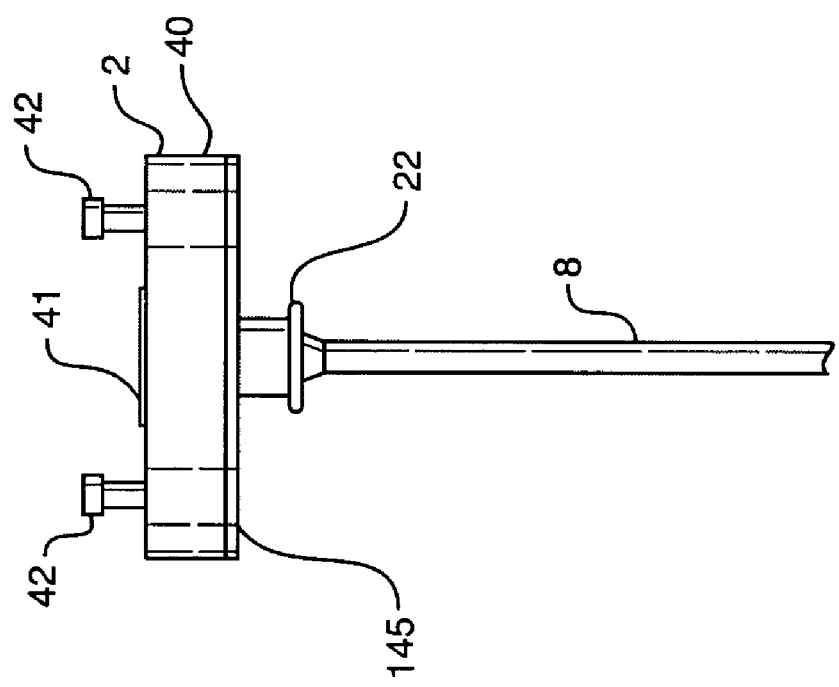

FIG. 3 depicts the introducer sheath 2. The introducer sheath 2 is placed into a ventricle of the brain 6 through craniotomy hole 23 (FIG. 1) with stereotaxic access needle 39 (FIG. 4) and probe 1 is then placed into the ventricle of the brain 6 through the introducer sheath 2. The introducer sheath 2 provides for access to a ventricle by standard stereotaxic surgical methods, and allows for removal and replacement of probe 1 during the course of the treatment. Introducer sheath 2 consists of sheath tube 8, housing 40, antiseptic pad 145, and probe docking pins 42. Fixation plug 22, and probe sealing boss 41 are formed integrally with the introducer housing 40. The fixation plug 22 works integrally with probe 1 to fixate the assembly to the head, and seal the craniotomy hole 23. The probe sealing boss 41 mates with the bottom surface of docking collar 24 of probe 1 and seals the assembly to prevent contamination and infection.

Figure 4:
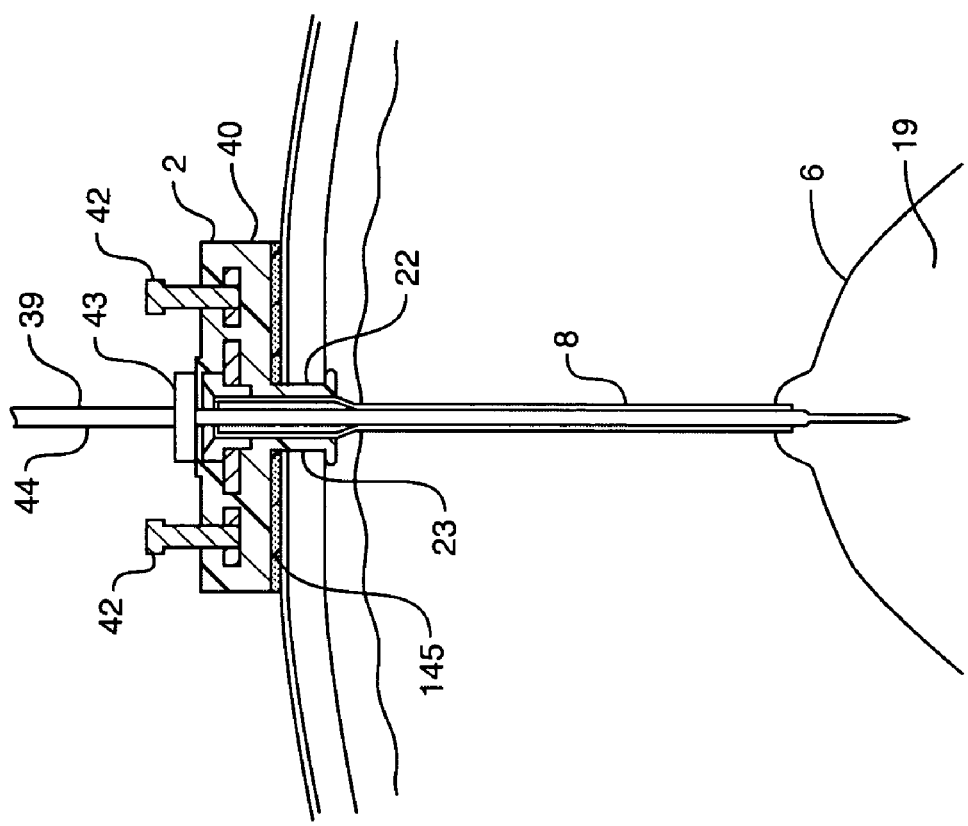
FIG. 4 shows a sectional view of the introducer sheath placement into a ventricle of the brain with the stereotaxic ventricle access needle.
Figure 5:
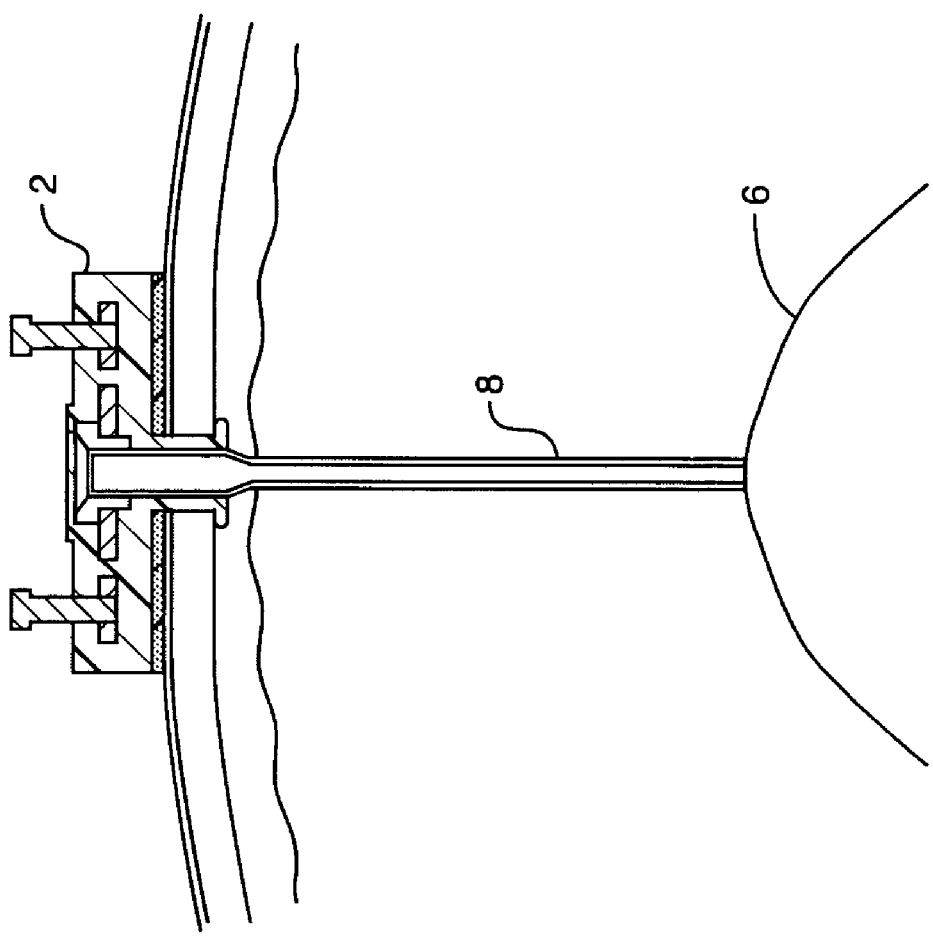
FIG. 5 shows a sectional view of the introducer sheath in operational position after the stereotaxic access needle has been removed.

FIG. 4 depicts introducer sheath 2 placement into ventricle 6 with the stereotaxic access needle 39. The diameter of the stereotaxic access needle 39 is tapered at the distal tip to the diameter of the probe shaft 21 as shown. Proximal to the taper, the diameter of the stereotaxic needle 39 is sized to slidably fit the inside diameter of the introducer tube 8. Needle stop 43 pushes the introducer sheath into ventricle 6 when the stereotaxic access needle 39 is advanced. The proximal end 44 of the stereotaxic access needle 39 is configured to function with various commercial stereotaxic needle guidance systems (not shown). FIG. 5 depicts the introducer sheath 2 in ventricle 6 after the stereotaxic access needle 39 (FIG. 5) is removed.

FIG. 6 depicts in schematic form the integral operation of probe 1, cooling assembly 3 and control consol 76. The functional components of probe 1 are probe shaft 21, fluid port 26, and thermocouple 18. The functional components of the cooling assembly are cooling cylinder 72, piston 48, cooling coil assembly 47, and thermocouple 45. The control console 76 contains control circuitry 53, motor shaft position transducer 54, motor 55, crank 56, connecting rod 57, pneumatic cylinder 58, piston 59, AC power source 60, Transformer 61, low-pressure solenoid valve 63, high-pressure solenoid valve 64, low-pressure line 65, low-pressure pneumatic line 68, umbilical connector 69, high pressure gas connector/valve 71, low-pressure gas connector/valve 73, and user control panel 74. The basic operation (after probe 1 and introducer sheath 2 is placed in operational position as previously described, and the system has been purge of air as described in detail below) is as follows:

1) Cerebrospinal fluid 19 (FIG. 1) is drawn into cooling cylinder 72 of cooling assembly 3 through fluid port 26 and probe shaft 21 by movement of piston 48 from position (1) (shown in dashed lines) to position (2) (shown in solid lines). (Cooling cylinder 72 of cooling assembly 3 is connected to pneumatic cylinder 58 of control console 76 by pneumatic gas line 37. Pneumatic piston 59 is actuated from position (1) (shown in dashed lines) to position (2) (shown in solid lines) by crank 56, connecting rod 57, and motor 55. Pneumatic coupling between cooling cylinder 72 and pneumatic cylinder 58 causes piston 48 to move from position (1) to position (2) when pneumatic piston 59 is actuated from position (1) to position (2).)

2.) High-pressure solenoid valve 64 is opened allowing high pressure gas to enter cooling coil assembly 47. Cerebrospinal fluid 19 contained in cooling cylinder 72 is then cooled by cooling coil assembly 47 by thermal conduction of heat through the walls of cooling cylinder 72 into cooling coil assembly 47. (Detailed description of cooling mechanism is described in description of FIG. 8 below).

3.) When the cerebrospinal fluid 19 in cooling cylinder 72 is cooled to predetermined temperature (5 Deg. C. to 30 Deg. C.) as sensed by thermocouple 45 of cooling assembly 3, high-pressure solenoid valve 64 is closed thereby stopping the cooling process, and pneumatic piston 59 is actuated from position (2) to position (1) causing piston 48 to move from position (2) to position (1) which reintroduces the cooled cerebrospinal fluid into ventricle 6.

4.) After a predetermined time to allow for thermal diffusion (5 to 60 seconds) the temperature of the cerebrospinal fluid 19 in ventricle 6 is measured by thermocouple 18. If after this period of time the temperature of the cerebrospinal fluid 19 in ventricle 6 is above a predetermined temperature (20 Deg. C. to 35 Deg. C.) the cycle (steps 1–3 above) is repeated. If the temperature of the cerebrospinal fluid 19 in ventricle 6 remains at or below the predetermined temperature after the time allowed for thermal diffusion, ventricle temperature is continuously monitored by thermocouple 18. The cycle (steps 1–3 above) is repeated once the temperature of the cerebrospinal fluid 19 in ventricle 6 rises above the predetermined value as described above.

Figure 8:
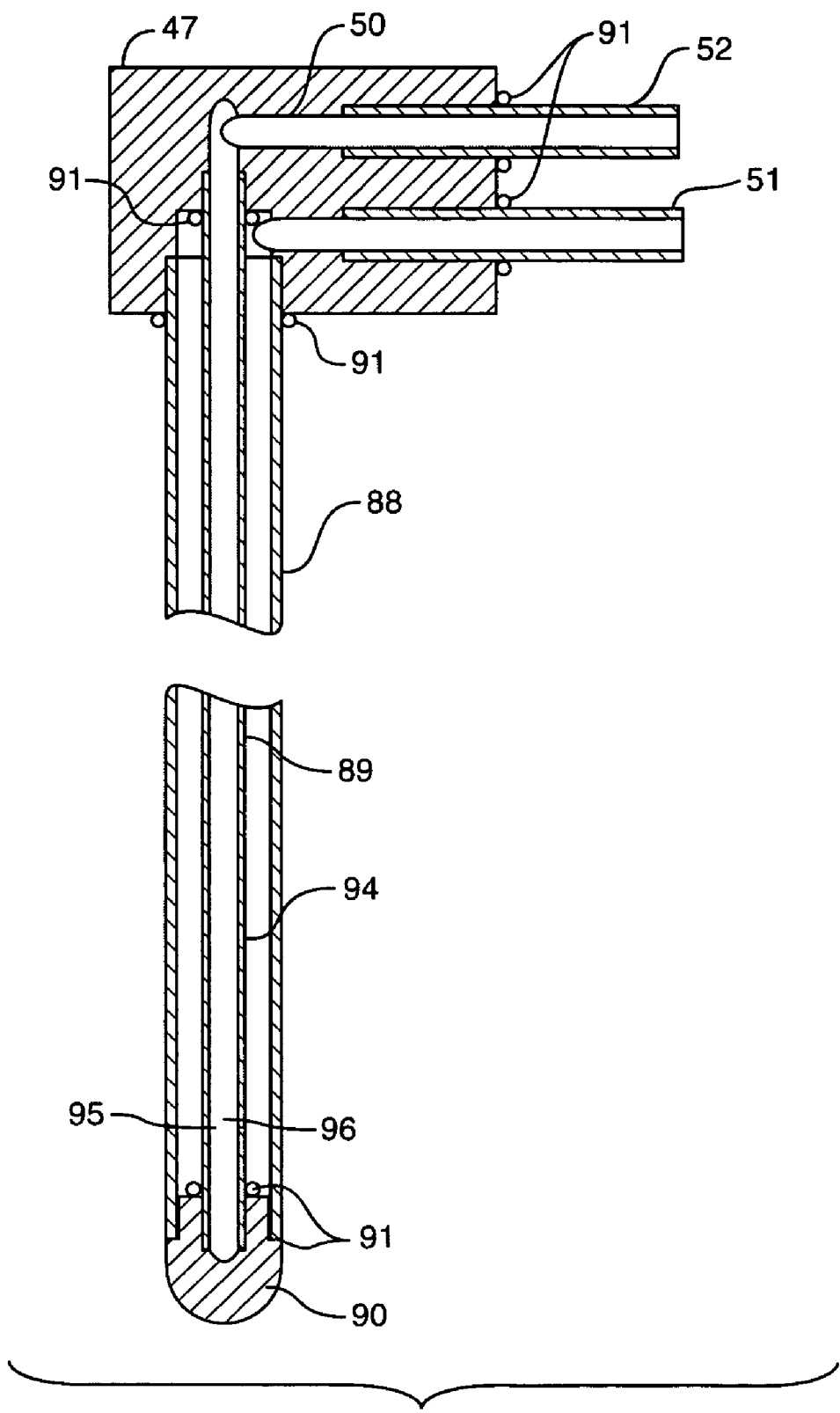
FIG. 8 shows a sectional view of the cooling coil prior to formation of the coil.

Cooling coil assembly 47 removes heat from cooling cylinder 72 by a cooling process commonly known as Joule-Thompson effect where gas (nitrogen, argon, or a mixture of nitrogen and argon) is expanded from a high-pressure to low-pressure within the cooling coil assembly 47 (FIG. 8). Cooling gas is supplied to cooling coil assembly 47 from the control console 76 at a pressure between 200 pounds per square inch absolute (PSIA) and 1600 PSIA by high-pressure tube 35 contained in umbilical 14 (FIGS. 1 & 2). Expanded low-pressure gas (5 to 100 PSIA) is returned to the control console 76 by low-pressure tube 36 contained in umbilical 14. Prior to use, the probe 1 and cooling assembly 3 is connected to the control consol 76 by umbilical 14 and umbilical connector 69 (shown in schematic form). After connecting umbilical 14 to control console 76 the system is purged of air, and cooling piston 48 is moved into position 1 as follows:

1.) Pneumatic piston 59 is moved into position (1) by motor 55, crank 56, and connecting rod 57. Position transducer 54 provides control circuitry 53 with a signal indicative of pneumatic piston 59 position.

2.) High-pressure solenoid valve 64 is then opened allowing cooling gas to flow into cooling coil assembly 47 at high pressure, and cooling gas to flow from cooling coil assembly 47 at low pressure back to the control console thereby displacing air from cooling coil 47, and gas lines 35, 36, 65, and 66.

3.) After a predetermined period of time (20 to 60 seconds) to allow for complete purging of air, low-pressure solenoid valve 63 is opened forcing cooling piston 48 into position (1). Low-pressure solenoid valve 63 is then closed, leaving both pneumatic piston 59, and cooling piston 48 in position (1).

4.) Probe 1 is then placed into brain ventricle 6 as previously described and cerebrospinal fluid 19 is drawn from ventricle 6 by syringe (not shown) through fluid tube 15 and luer fitting 25 (FIG. 2A) to remove air from probe shaft 21.

Control console 76 is connected to a source of high-pressure cooling gas by high-pressure valve/connector 71. Low-pressure gas is vented to the room trough low-pressure valve/connector 73. Electrical power is supplied to the control console by power source 60, which is normally an AC wall outlet. Transformer 61 transforms voltage from local standard AC voltage (120 or 240 volts) to system operating voltage (5 to 21 V). Control circuit 53 contains rectifier circuitry to transform source voltage from AC to DC. User control panel 74 contains user controls and operational display of system function. The user control panel provides for a means to set the desired temperature of the cerebrospinal fluid 19 in ventricle 6, a means to display the temperature of cerebrospinal fluid 19 in ventricle 6, a means to set the duration for cooling the cerebrospinal fluid 19 in ventricle 6, a means to set the rate of cooling and rewarming of cerebrospinal fluid 19 in ventricle 6, a means to initiate the air purge cycle as described above, and a means to turn the cooling cycle on and off. It obvious to those skilled in the art of electronic design how to design the electronic circuits, user controls, and how to specify the appropriate components to provide system functionality as described above. Those familiar with the art of mechanical design know how to design the pneumatic cylinder 58, to design the pneumatic piston 59 actuation mechanisms, to specify the appropriate motor 55 and position transducer 54, to specify the appropriate valves 71, 73, 64, & 63, to specify the appropriate gas lines 65, 66, and 68, and how to physically integrate all system components into a console configuration to provide system functionality as described above.

DESCRIPTION FIGS. 7–18—PREFERRED CONSTRUCTION EMBODIMENTS

Figure 7:
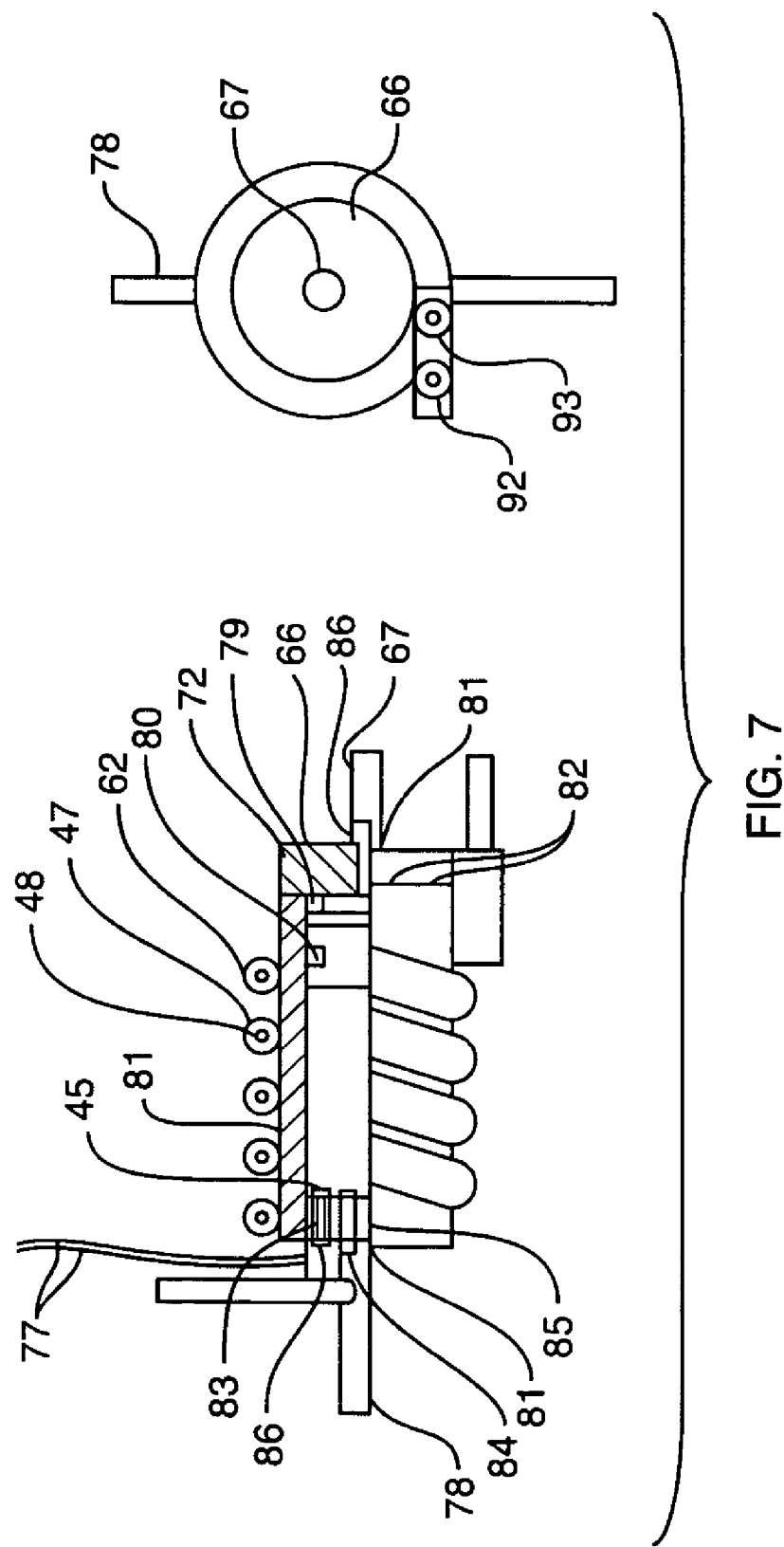
FIG. 7 shows a partial sectional view of the cooling assembly.

FIG. 7 depicts in a partial sectional view the cooling cylinder sub-assembly 62 of cooling assembly 3. Cooling cylinder sub-assembly 62 consists of cooling cylinder 72, piston 48, cylinder cap 66, pneumatic stem 67, cooling coil assembly 47, thermocouple 45, thermocouple leads 77, fluid manifold 78, O-ring 79, O-ring 80, and silver solder 81. Cylinder 72, and cylinder cap 66 are machined from a copper allow to maximize thermal heat transfer to cooling coil assembly 47. After machining, cylinder 72 and cylinder cap 66 are plated with gold to provide for biocompatibility. Cylinder 72 has an inner diameter between 0.4 inches and 1.0 inches. Cylinder 72 has a wall thickness between 0.02 inches and 0.1 inches. The length of cylinder 72 is between 1.5 and 4 inches. The displacement of piston 48 in cylinder 72 is between 1 cc and 5 cc. Piston 48 is machined or molded from a medical grade polymer such as nylon, but may also be machined from a metal alloy. The outer diameter of piston 48 is between 0.001 and 0.015 inches smaller than the inner diameter of cylinder 72. O-Ring 80 pneumatically isolates one side of piston 48 from the opposite side, and resides in an appropriately sized gland formed in piston 48 as shown. The length of piston 48 is between 0.5 and 1.5 its outer diameter. The construction of cooling coil assembly 47 is described in detail in FIGS. (8 & 9). O-ring 79 resides in a gland formed in cylinder cap 66 during the machining process and provides for a pneumatic seal between the cylinder 72 and the cylinder cap 66. Fluid manifold 78 is formed from type 304 stainless steel tubing and provides for fluid connection between fluid tube 13 and fluid tube 15 (FIG. 1) and cylinder 72. The inner diameter of fluid manifold 78 is between 0.06 and 0.08 inches in diameter, and the walls of fluid manifold 78 are between 0.002 and 0.005 inches thick. Pneumatic stem is made from type 304 stainless steel and has an inner diameter of 0.08 to 0.12 inches in diameter and has a wall thickness of 0.002 to 0.005 inches thick. The cooling cylinder sub-assembly is assembled as follows: 1.) Fluid manifold 78 is inserted into end hole 85 in cylinder 72 and soldered into place with silver solder 81. 2.) Cooling coil assembly 47 is soldered to cylinder 72 with silver solder 81 as shown. 3.) Thermocouple 45 is inserted into cylinder end hole 83 and glued in place with silicon rubber adhesive 86. 4.) O-ring 80 is mounted to piston 48. Piston 48 is then inserted into cylinder 72. 5.) O-ring 79 is mounted on cylinder cap 66. Cylinder cap is then inserted into cylinder as shown and crimped into place with dimple crimps 82 as shown.

FIG. 8 depicts a sectional view of the construction of cooling coil assembly 47 prior to the coiling operation. Cooling coil assembly 47 consists of manifold 50, low-pressure tube 88, high-pressure tube 89, end cap 90, silver solder 91, high-pressure stub 52, and low-pressure stub 51. Manifold 50, and end cap 90 are machined from type 304 stainless steel as shown. Low-pressure tube 88, high-pressure tube 89, high-pressure stub 52, and low-pressure stub 51 are made from type 304 stainless steel tubing. Low-pressure tube 88 has an inner diameter of 0.09 to 0.12 inches, and has a wall thickness between 0.02 and 0.05 inches. High pressure tube 89 has a inner diameter of. 0.03 and 0.06 inches and has a wall thickness of 0.002 and 0.005. High-pressure stub 52 and low-pressure stub 51 have an inner diameter of 0.06 and 0.10 inches, and has a wall thickness of 0.002 to 0.005. High-pressure tube 89 has a least one hole drilled through the wall to form gas expansion orifice 96. Gas expansion orifice 96 is between 0.002 and 0.008 inches in diameter. Cooling coil assembly 47 is assembled as follows: 1.) High-pressure tube 89, and low pressure tube 88 are soldered to end cap 90 as shown with silver solder 91. 2.) High-pressure stub 52 and low pressure stub 51 are soldered to manifold 50 as shown with silver solder 91. 3.) Manifold 87 is then soldered to high-pressure tube 89 and low-pressure tube 88 as shown with silver solder 91. The length (from manifold 50 to end cap 90) of the cooling coil assembly 47 prior to coiling is between 3 and 8 inches. Gas at high pressure enters high-pressure tube 89 and forms high-pressure zone 95 through manifold 50 and high-pressure stub 52 and is expanded to a low pressure in low-pressure zone 94. Gas from low-pressure zone 94 is exhausted through manifold 50 and low-pressure stub 51, and ultimately to the room as previously described. During gas expansion from high pressure to low pressure heat is lost according to the Joule-Thompson principle causing the temperature of the expanded gas to be lowered, thereby cooling the walls of low-pressure tube 88 causing absorbs ion of heat from cooling cylinder 72 as previously described.

Figure 9:
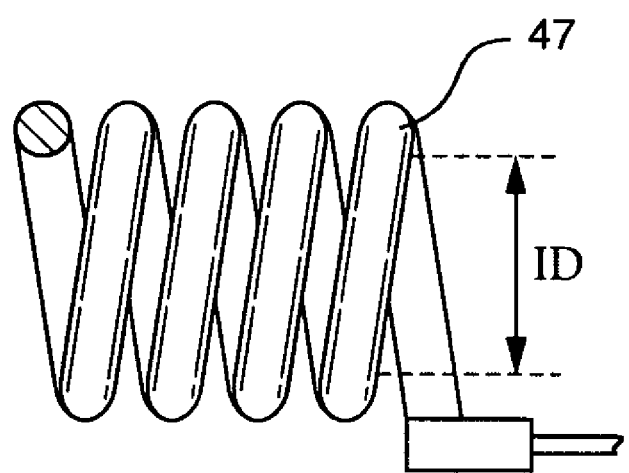
FIG. 9 shows the cooling coil after formation of the coil.

FIG. 9 depicts the cooling coil assembly 47 after coiling operation. The coiling accomplished by wrapping the assembly around a mandrel. The inner diameter of the coil in relaxed state is 0.010 to 0.030 inches smaller than the outside diameter of cooling cylinder 72 to ensure intimate contact between cooling coil assembly 47 and cooling cylinder 72.

FIG. 10A depicts a sectional view of the construction of the cooling assembly 3. FIG. 10B shows an end view of cooling assembly 3 prior to attachment of umbilical assembly 14. Cooling assembly 3 consists of cooling cylinder sub-assembly 62, probe 1 (see FIGS. 12A & 12B for construction details) cooling assembly housing 97, cooling assembly mounting plate 27 (See FIG. 18 for construction detail), mounting pads 28, fluid tube crimp ring 98, stop cock assembly 99 which consists of fluid tube 15, stop cock 19, and luer fitting 25, and crimp ring 100. Cooling assembly 3 is formed as follows: 1.) Fluid tube 13 of probe 1 is mounted to fluid manifold 78 of cooling cylinder sub-assembly 62 as shown, and is held in place with crimp ring 100. 2.) Cooling cylinder sub-assembly, probe 1, mounting plate 27 are mounted into injection mold and cooling assembly housing 97 is formed by standard injection molding process. Housing 97 may be made any suitable thermoplastic such as nylon or high density polyethylene. Stop cock assembly 99 which consists of fluid tube 15, stop cock 19, and luer fitting 25 is attached to manifold 78 and held in place with crimp ring 98. Stopcock assembly 99 is readily available from many OEM medical device suppliers. Mounting pads 28 are common rubber grommets and are inserted into mounting holes 102 in mounting plate 27. Holes 101 are then drilled and tapped.

Figure 11C:
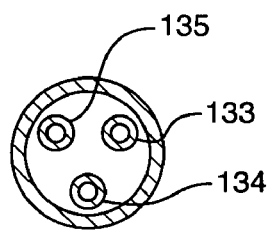
Figure 11D:
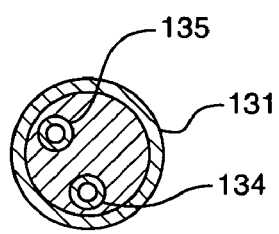
Figure 11E:
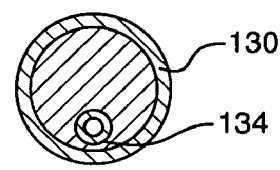
Figure 11F:
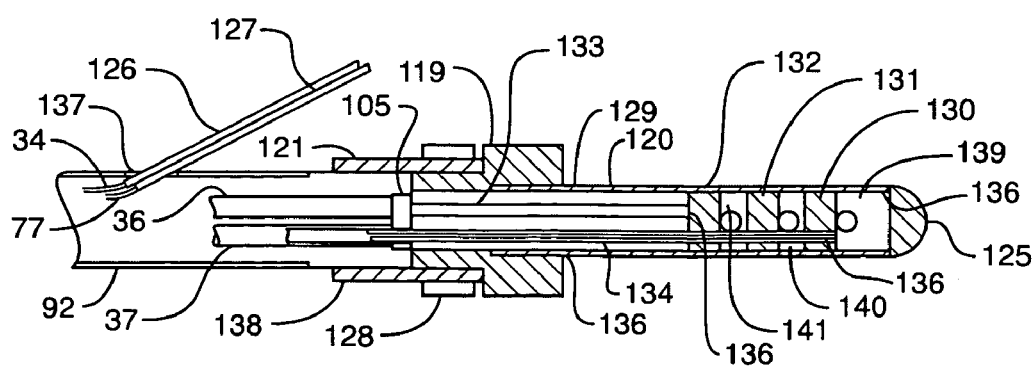

FIG. 11A depicts the attachment of the umbilical assembly 14 to the cooling assembly 3. FIG. 11B depicts the umbilical plug assembly 120. FIGS. 11C, 11D, and 11E depicts radial sections of umbilical plug assembly 120. FIG. 11F depicts a transverse section of umbilical plug assembly 120. FIG. 11G depicts the removable connection mechanism of umbilical assembly 14 to control console 76. Umbilical assembly 14 consists of umbilical flange 161, umbilical sheath 92, umbilical plug assembly 120, thermocouple connectors 107 and 108, high-pressure tube 35, low-pressure tube 36, pneumatic tube 37, thermocouple lead 34, thermocouple lead 77, thermocouple lead sheath 126 and 127, sheath retainer 121, tube crimp rings 105, silicone rubber compound 104, screw 103, and epoxy adhesive 106. The umbilical assembly 14 is between 3 and 8 feet long. The umbilical sheath 92 is vinyl tubing with an inner diameter of 0.25 to 0.375 inches and has a wall thickness of 0.010 to 0.025 inches. Umbilical flange 161 is injection molded from a suitable thermoplastic such as nylon. One end of umbilical sheath 92 is attached to umbilical flange 161 with epoxy adhesive 106 as shown. High pressure tube 35 is 0.125 to 0.31 inches in outer diameter and has a wall thickness of 0.025 to 0.040 inches in diameter and is made from nylon. Low-pressure tube 36, and pneumatic tube 37 are 0.125 to 0.31 inches in outer diameter with a wall thickness of 0.010 to 0.015 inches and are made of nylon. Parker Hannifin Corp. manufactures a full line suitable tubing under the brand name Parflex that is suitable for use for tubes 35, 36 and 37. Thermocouple leads 34 and 77 are selected for compatibility with thermocouples 45 and 18. Omega Corp. manufactures thermocouples, and thermocouple leads suitable for the application. Tubes 35, 36, and 37, and thermocouple leads 34 and 77 inserted into umbilical sheath 92 such that tubes 35, 36 and 37, and thermocouple leads 34 and 77 protrude past both ends of umbilical sheath 92 and umbilical flange 161 2 to 3 inches. High-pressure tube 35 is attached to high-pressure stub 52 of cooling assembly 3 and crimped into place with stainless steel crimp ring 105. Low-pressure tube 35 is attached to low-pressure stub 51 of cooling assembly 3 and crimped into place with stainless steel crimp ring 105. Pneumatic tube 37 is attached to pneumatic stub 67 of cooling assembly and crimped into place with stainless steel crimp ring 105. Thermocouple leads 34 and 77 are spot welded to thermocouple leads from thermocouple 18 and 45 respectively, and silicone rubber 104 is used to electrically insulate the weld joints. Umbilical flange 161 is then bolted to cooling assembly 3 with screws 103. Plug assembly 120 is attached to the opposite end the umbilical assembly 14 and provides removable connection of the cooling assembly 3 to the control console 76. FIGS. 11B–11F depicts the plug assembly 120. Plug assembly 120 consists of: plug tube 129, end cap 125, plug handle 119, sheath retainer 121, crimp ring 128, bulkhead 130, bulkhead 131, bulkhead 132, pneumatic tube 134, low-pressure tube 133, high-pressure tube 135, crimp ring 105, thermocouple lead sheath 126 & 127, thermocouple connectors 107 and 108, vinyl adhesive 137, epoxy adhesive 138, silver solder 136. Bulkhead 130 and end cap 125 form pneumatic gas chamber 139, bulkhead 130 and bulkhead 131 form high pressure gas chamber 140, bulkhead 131 and bulkhead 132 form low-pressure gas chamber 141. Pneumatic tube 134 connects pneumatic tube 37 to pneumatic gas chamber 139. High-pressure tube 135 connects high-pressure tube 35 to high-pressure gas chamber 140. Low-pressure tube 133 connects low-pressure tube 36 to low-pressure chamber 141. Pneumatic port 124, high-pressure port 123, and low-pressure port 122 provide gas communication with console receptacle 110 (FIG. 11G). Bulkheads 130, 131, 132, end cap 125, and plug handle are machined from type 304 stainless steel. Pneumatic tube 134, low-pressure tube 133, and high-pressure tube 135 are stainless steel with 0.125 to 0.187 inch outer diameter with 0.010 to 0.020 wall thickness. Plug tube 129 is soldered to plug handle 119 with silver solder 136. End cap 125 is soldered to plug tube 129 with silver solder 136. Bulkhead 130, is soldered to pneumatic tube 134 with silver solder 136. Bulkhead 131 is silver soldered to pneumatic tube 134 and high-pressure tube 135. Bulkhead 132 is soldered to pneumatic tube 134, high-pressure tube 135, and low-pressure tube 133. The soldered assembly described above is inserted into plug tube 129 as shown and is swaged by a rotary swager to form a seal between bulkheads 130, 131, and 132 and plug tube 129. Thermocouple leads 34 and 77 exit umbilical sheath 92 approximately 6 inches from umbilical plug assembly 120 and are reinforced with vinyl sheaths 126 and 127 whch are retained by vinyl adhesive 137 as shown. Pneumatic tube 37 is attached to pneumatic tube 134 with crimp ring 105. High-pressure tube 35 is attached to high-pressure tube 135 with crimp ring 105. Low-pressure tube 36 is attached to low-pressure tube 133 with crimp ring 105. Vinyl sheath retainer 121 is glued to umbilical sheath 92 with epoxy 138, and fixated to plug handle 119 with stainless steel crimp ring 128. FIG. 1G depicts the construction of the control console 76 plug receptacle assembly 110 in functional relationship with umbilical plug assembly 120. Plug receptacle assembly 110 consists of: manifold 142, pneumatic stem 115, high-pressure stem 117, low-pressure stem 118 and O rings 114, 113, 112, and 111. Stems 115, 117 and 118 are stainless steel tubes 0.125 to 0.187 inch outer diameter with 0.010 to .o15 wall thickness. Stems 115, 117, and 118 are silver soldered to manifold 142 with silver solder 116 as shown. O-rings 114 and 113 provide gas communication to console 76 pneumatic line 68 as shown. O-rings 113 and 112 provide gas communication to console 76 high-pressure line 65 as shown. O-rings 112 and 111 provide gas communication to console 76 low-pressure line 66 as shown. Plug receptacle assembly 110 is mounted to control console 76 control panel 74 with hardware as shown. Thermocouple leads 34 and 77 are connected to the control console by standard thermocouple plugs 107 and 108 vie standard thermocouple receptacles (not shown).

FIG. 12A depicts a sectional view of probe 1. FIG. 12B depicts a sectional view of probe shaft 21. Probe 1 consists of shaft 21, probe tube 13, sheath docking collar 24, sheath expansion plug 29, thermocouple 18, and thermocouple lead 34. Probe shaft 21 is extruded from high density polyethylene and has two lumens. Lumen 32 is the cerebrospinal fluid 19 channel. Lumen 33 contains thermocouple leads 34 and thermocouple 18 at distal end 7. Probe shaft 21 is 1.0 to 1.5 mm in diameter. Lumen 32 is 0.7 to 1.0 mm in diameter. Lumen 33 is 0.2 to 0.3 mm in diameter. The length of probe shaft is 3 to 10 cm. Distal end 7 is closed by melting process commonly referred to as tip forming by those skilled in the art catheter making. A stainless steel mandrel occupies lumen 32 during the tip forming process which maintains the shape of lumen 32 as shown. Thermocouple 18 is secured during tip forming by melting and collapsing lumen 33. A milling process forms fluid port 26. Sheath docking collar 24 is injection molded of a nylon compound. Sheath expansion plug 29 is stainless steel tubing who's inside diameter is equal to the outside diameter of probe shaft 21 and has a wall thickness of 0.015 to 0.030 inches. Sheath expansion plug 29 is integrated with sheath docking collar 24 by insert molding technique during molding process. Fluid tube 13 is a continuation of probe shaft 21. Probe shaft 21 and fluid tube 13 are fastened to sheath docking collar 24 and sheath expansion plug 29 with adhesive 143.

FIG. 13 shows a bottom view of probe 1 depicting the sheath/housing docking mechanism. Introducer sheath docking pins 42 (FIG. 3) enter pinhole 93 in docking collar 24. The probe 1 is then rotated 45 degrees in the direction shown to lock probe 1 to introducer sheath 2.

FIG. 14 depicts a sectional view of the introducer sheath 2. The introducer sheath consists of the sheath/probe docking ring assembly 147 (See FIG. 15 for construction details), introducer sheath tube assembly 144 (See FIG. 16 for construction details) Antiseptic pad 145, and introducer sheath housing 40. The introducer sheath assembly, except the antiseptic pad is formed by placing the sheath/probe docking ring assembly 147, and introducer sheath tube assembly 144 into a fixturing mold and casting the introducer sheath housing 40 to form the integrated assembly. The introducer sheath housing 40 is cast from a two-part medical grade silicon rubber with a hardness of between 40 and 60 durometer. Dow-Corning Corporation manufactures a full line of medical grade silicon rubber suitable for this application. The antiseptic pad 145 is made from open cell foam, and is saturated with antiseptic fluid either at the factory, or in the field prior to use. Antiseptic foam pad 145 is between 10 and 20 durometer in hardness. A suitable antiseptic fluid is an iodine solution marketed under the registered trade name Betadine. The foam pad 145 may be glued to the bottom face of the introducer housing 40 with a suitable adhesive.

FIG. 15A shows a sectional view of the sheath/probe docking ring assembly 147. The sheath/probe docking ring assembly 147 consists of type 304 stainless steel docking ring 148 and two type 304 stainless steel docking pins 42. The docking ring 148 has a hole in the center which mates with the sheath tube assembly 144 as shown in FIG. 14. The docking ring has (6) holes 149 which provides anchorage within the introducer sheath housing 40 when the introducer sheath housing 40 is molded around the sheath/probe docking assembly 147. The docking pins 42 are welded to the docking ring 148.

FIG. 16 shows a sectional view of the introducer sheath tube assembly 144. The introducer sheath tube assembly 144 consists of the sheath tube 8, and the sheath ferrule 150. The sheath tube 8 and the sheath ferrule 150 are made of high density polyethylene or other suitable thermoplastic. The sheath tube is extruded into tubular form by standard means, and then blow molded into final shape. The wall thickness of the sheath tube 8 is between 0.001 and 0.002 inches. The inside diameter of the sheath tube 8 at the distal end is 0.020 to 0.025 inches greater than the diameter of the probe shaft 21 it is designed to mate with. The inside diameter of the sheath tube at the proximal end is 0.001 to 0.004 inches smaller than the sheath expansion plug 29 of probe 1 that it is designed to mate with. The sheath ferrule 150 is injection molded and is bonded to sheath tube 8 by standard ultrasonic welding techniques.

FIGS. 17a and 17B depicts the system control console 76. The control console 76, contains a source for cooling gas (argon or nitrogen) in multiple, replaceable tanks 151. The gas tanks 151 are connected to the console 76 using common medical grade pressure regulators 152. The control console 76 has a control panel 74, which provides for cerebrospinal fluid 19 temperature display means 158, and a means to display relative cooling power (0% to 100% of maximum heat removal capacity) 159. The control panel has a means to adjust the cerebrospinal fluid 19 temperature setting 160. The control console may be constructed to provide for operation of multiple probes 1 simultaneously by means of multiple display and control channels 157. The control console 76 has means to removably connect the probe umbilical 14 to the control console, where the connection means is by gas plug 120 on the end of the probe umbilical cable 14, and gas plug receptacle 110 mounted on the front of the control panel 74. The control console also provides an electrical connection means for the probe tip thermocouple leads 34 and 77 by the thermocouple receptacle 154 and 155 on the control panel 74.

FIG. 18 depicts the construction of mounting plate 27. Mounting plate 27 is made from stainless steel sheet and is 0.005 to 0.010 inches thick.

Alternate Embodiments

A fluid pump may be used, instead of a syringe mechanism as described in the preferred embodiment, in conjunction with a probe that contains 2 fluid channels, or multiple probes, to continuously remove, replace and cool cerebrospinal fluid. The cerebrospinal fluid cooling mechanism may placed in the control console, or further away from the head than as described in the preferred embodiment. The method of cooling may be other than Joule-Thompson effect.

Advantages

From the description above there are a number of advantages my method and apparatus for treating secondary brain injury provide:
 (a) The therapeutic agent (hypothermia) for preventing secondary injury according to this invention is applied directly to the brain.
 (b) The therapeutic agent (hypothermia) for preventing secondary injury according to this invention is limited to the brain.
 (c) Lower hypothermic temperatures can be practically achieved in the brain than can be achieved by the methods currently described in the art since only the brain is exposed to hypothermia.
 (d) Lower hypothermic temperatures can be achieved in the brain than with methods described in the art.
 (e) Hypothermic temperatures can be maintained longer in the brain than with methods described in the art.
 (f) Hypothermic temperatures can be achieved in the brain by means of a single small caliber-cooling probe.
 (g) The degree of hypothermia in the brain can be adjusted according to the physiological response to hypothermia.
 (h) Ventricle cooling may be accomplished without introducing extra-corporeal fluids.

I claim:
1. A method for reducing secondary brain injury comprising the steps of:
 (a) placing an elongated probe comprising a distal end, a proximal end, a cooling assembly in the vicinity of said proximal end, and a means to communicate fluid between said distal end and said proximal end and said cooling assembly, into a brain ventricle so that said distal end resides in a brain ventricle, and that said proximal end and said cooling assembly reside ex-vivo, then (b) transferring a portion of the cerebrospinal fluid within said brain ventricle into said cooling assembly, then (c) cooling said cerebrospinal fluid within said cooling assembly, then (d) transferring said cerebral spinal fluid from said cooling assembly back into said brain ventricle, thereby cooling at least a portion of the brain, wherein the volume of said cerebrospinal fluid removed from, cooled, and then returned to said brain ventricle is between about 1 and 20 milliliters per cycle.

2. The method of claim 1 wherein said cooling assembly is located in close proximity to the head of the patient.

3. The method of claim 2 wherein said cooling assembly is fastened to said head.

4. The method of claim 1 where steps (a) through (d) are repeated in a cyclical manner.

5. The method of claim 4 wherein the rate at which steps (a) through (d) is repeated is between about 10 and 120 times per minute.

6. The method of claim 1 where steps (a) through (d) are accomplished in a continuous manner.

7. The method of claim 6 wherein the volumetric rate at which said cerebrospinal fluid is cooled is between about 10 and 120 milliliters per minute.

8. The method of claim 1 wherein said cerebrospinal fluid contained in said brain ventricle is cooled to a predetermined temperature.

9. The method of claim 8 wherein said temperature of said cerebrospinal fluid is maintained at said predetermined temperature for a predetermined period of time.

10. The method of claim 1 wherein said brain ventricle is a lateral ventricle.

11. The method of claim 1 wherein said probe substantially comprises a flexible catheter.

12. The method of claim 1 wherein a single said probe is placed into a single said brain ventricle to reduce secondary brain injury.

13. The method of claim 1 wherein a plurality of said probes is placed into a plurality of said brain ventricles to reduce secondary brain injury.

14. A brain-cooling probe comprising:
(a) a flexible elongated structure which includes a distal end, and a proximal end, the proximal end of the flexible elongated structure comprising a coupling assembly configured to couple the proximal end of the brain-cooling probe to a patient's head,
(b) a cooling assembly located in the vicinity of said proximal end comprising a fluid cooling means and a fluid pumping means,
(c) a means for communicating fluid between said distal end, said proximal end, and said cooling assembly,
(d) a means for connecting said brain-cooling probe to a control console, whereby said distal end is constructed to provide a means for placement of said distal end into a brain ventricle by standard surgical technique, and where said proximal end and said cooling assembly are constructed to remain ex-vivo in close proximity to the patient's head, and said fluid cooling means comprises a means to transfer heat from cerebrospinal fluid contained within said cooling assembly to cooling fluid supplied by said control console whereby physical separation between said cerebrospinal fluid and said cooling fluid is maintained by said heat transfer means.

15. The brain-cooling probe of claim 14 wherein said flexible elongated structure is substantially a catheter with an outer diameter of about 3 millimeters.

16. The brain-cooling probe of claim 14 wherein said fluid pumping means comprises a means for transferring cerebrospinal fluid from a brain ventricle into said cooling assembly, and a means to transfer said cerebrospinal fluid from said cooling assembly back into said brain ventricle.

17. The brain-cooling probe of claim 14 wherein said means for communicating fluid comprises at least one fluid channel between said distal end and said proximal end and said cooling assembly, and at least one fluid port in the vicinity of said distal end.

18. A system for reducing secondary brain injury comprising:
(a) at least one brain-cooling probe comprising a flexible elongated structure which includes a distal end constructed to provide a means for placement of said distal end into a brain ventricle, a proximal end having a coupling assembly configured to couple the proximal end of the brain-cooling probe to a head associated with the brain ventricle, and a cooling assembly located in the vicinity of said proximal end with said cooling assembly comprising a fluid cooling means and a fluid pumping means, a means for communicating fluid between said distal end and said proximal end and said cooling assembly, and a means to connect said brain-cooling probe to a control console,
(b) a control console comprising a means of supplying cooling fluid to said cooling assembly of at least one said brain-cooling probe, a means of actuating said fluid pumping means of said cooling assembly of at least one said brain-cooling probe, and a means to control said brain cooling by at least one said brain-cooling probe.

19. A brain probe assembly comprising:
a probe defining a lumen, the probe having a distal end and a proximal end, the distal end of the probe configured to insert within a ventricle of a brain; and
a cooling assembly coupled with the proximal end of the probe, the cooling assembly having:
a pump in fluid communication with the lumen defined by the probe, the pump configured to remove fluid from the ventricle of the brain and return the fluid to the ventricle of the brain via the lumen defined by the probe, the pump having a cylinder defining a chamber configured to contain fluid from the ventricle of the brain as the pump removes fluid from the ventricle of the brain, via the lumen defined by the probe; and
a cooling coil assembly in thermal communication with the cylinder of the pump, the cooling coil assembly configured to receive a cooling fluid and reduce a temperature of the fluid removed from the ventricle of the brain by the pump.

20. The brain probe assembly of claim 19 further comprising a sheath defining a sheath tube, the sheath configured to insert within a brain and the sheath tube configured to receive the probe to provide the probe with access to the ventricle.

21. The brain probe assembly of claim 20 wherein the sheath comprises a housing coupled to a proximal end of the sheath tube and an antiseptic pad coupled to the housing, the antiseptic pad configured to orient between the housing and a skull associated with the brain.

22. The brain probe assembly of claim 19 wherein the probe comprises a temperature sensor configured to orient in thermal communication with the fluid of the ventricle.

23. The brain probe assembly of claim 19 further comprising a drainage assembly in fluid communication with the lumen defined by the probe.

24. The brain probe assembly of claim 19 further comprising a pressure sensor oriented at the distal end of the probe.

25. A brain probe system comprising:
a brain probe assembly having:
   a probe defining a lumen, the probe having a distal end and a proximal end, the distal end of the probe configured to insert within a ventricle of a brain, and
   a cooling assembly coupled with the proximal end of the probe, the cooling assembly having:
      a pump in fluid communication with the lumen defined by the probe, the pump configured to remove fluid from the ventricle of the brain and return the fluid to the ventricle of the brain via the lumen defined by the probe, the pump having a cylinder defining a chamber configured to contain fluid from the ventricle of the brain as the pump removes fluid from the ventricle of the brain, via the lumen defined by the probe, and
      a cooling coil assembly in thermal communication with the cylinder of the pump, cooling coil assembly configured to receive a cooling fluid and reduce a temperature of the fluid removed from the ventricle of the brain by the pump; and
a console coupled to the brain probe assembly, the console configured to circulate a cooling fluid through the cooling coil assembly.

26. The brain probe system of claim 25 further comprising a sheath defining a sheath tube, the sheath configured to insert within a brain and the sheath tube configured to receive the probe to provide the probe with access to the ventricle.

27. The brain probe system of claim 26 wherein the sheath comprises a housing coupled to a proximal end of the sheath tube and an antiseptic pad coupled to the housing, the antiseptic pad configured to orient between the housing and a skull associated with the brain.

28. The brain probe system of claim 25 wherein the probe comprises a temperature sensor configured to orient in thermal communication with the fluid of the ventricle, the temperature sensor being electrically coupled to the console.

29. The brain probe system of claim 25 further comprising a drainage assembly in fluid communication with the lumen defined by the probe.

30. The brain probe system of claim 25 further comprising a pressure sensor oriented at the distal end of the probe.

31. A method for inducing cerebral hypothermia comprising:
introducing a distal end of a probe, associated with a brain probe assembly, within a ventricle of a brain, the probe defining a lumen;
measuring a temperature of the fluid within the ventricle of the brain;
removing, via a cooling assembly associated with the brain probe assembly and in fluid communication with the lumen of the probe, fluid from the ventricle of the brain;
reducing a temperature of the fluid removed from the ventricle of the brain; and
returning the fluid to the ventricle of the brain via the lumen defined by the probe.

32. The method of claim 31 further comprising the steps of:
comparing the temperature of the fluid within the ventricle of the brain to a target temperature; and
repeating the steps of removing, reducing, and returning until a temperature of the fluid within the ventricle of the brain is substantially equal to the target temperature.

33. The method of claim 31 further comprising:
measuring a pressure of the fluid within the ventricle of the brain;
adjusting a temperature of the fluid within the ventricle of the brain based upon the measured pressure.

34. The method of claim 31 further comprising maintaining a temperature of a body associated with the brain.

35. A brain probe assembly comprising:
a sheath defining a sheath tube having a distal end and a proximal end, the distal end of the probe configured to insert within a ventricle of a brain and the proximal end configured to couple to a head of the brain;
a probe defining a lumen, the probe having a distal end and a proximal end, the distal end of the probe configured to insert within the sheath tube to access the ventricle of the brain and the proximal end configured to couple to the proximal end of the sheath tube; and
a cooling assembly coupled with the proximal end of the probe, the cooling assembly having:
   a pump in fluid communication with the lumen defined by the probe, the pump configured to remove fluid from the ventricle of the brain and return the fluid to the ventricle of the brain via the lumen defined by the probe, and
   a heat transfer assembly in thermal communication with the pump, the heat transfer assembly configured to reduce a temperature of the fluid removed from the ventricle of the brain by the pump.

36. The brain probe assembly of claim 35 wherein the probe defines a single lumen and wherein the pump is configured to remove fluid from the ventricle of the brain via the single lumen defined by the probe and return the fluid to the ventricle of the brain via the single lumen defined by the probe.

37. The brain probe assembly of claim 35 wherein the distal end of the probe comprises a temperature sensor configured to orient within the ventricle in thermal communication with the fluid of the ventricle.

38. A brain probe system comprising:
a brain probe assembly having:
   a sheath defining a sheath tube having a distal end and a proximal end, the distal end of the probe configured to insert within a ventricle of a brain and the proximal end configured to couple to a head of the brain, and
   a probe defining a lumen, the probe having a distal end and a proximal end, the distal end of the probe configured to insert within the sheath tube to access the ventricle of the brain and the proximal end configured to couple to the proximal end of the sheath tube, and
   a cooling assembly coupled with the proximal end of the probe, the cooling assembly having:
      a pump in fluid communication with the lumen defined by the probe, the pump configured to remove fluid from the ventricle of the brain and return the fluid to the ventricle of the brain via the lumen defined by the probe, and a heat transfer assembly in thermal communication with the pump, the heat transfer assembly configured to reduce a temperature of the fluid removed from the ventricle of the brain by the pump; and a console coupled to the brain probe assembly, the console configured to circulate a cooling fluid through the heat transfer assembly.

39. The brain probe system of claim 38 wherein the probe defines a single lumen and wherein the pump is configured to remove fluid from the ventricle of the brain via the single lumen defined by the probe and return the fluid to the ventricle of the brain via the single lumen defined by the probe.

40. The brain probe system of claim 38 wherein the distal end of the probe comprises a temperature sensor configured to orient within the ventricle in thermal communication with the fluid of the ventricle.

41. The method of claim 1 comprising:
measuring a pressure of the fluid within the ventricle of the brain;
adjusting a temperature of the fluid within the ventricle of the brain based upon the measured pressure.

42. The method of claim 1 comprising coupling the proximal end of the probe to a head of the brain.

43. A method for inducing cerebral hypothermia comprising:

introducing a distal end of a probe, associated with a brain probe assembly, within a ventricle of a brain, the probe defining a lumen;

removing, via a cooling assembly associated with the brain probe assembly and in fluid communication with the lumen of the probe, fluid from the ventricle of the brain;

measuring a pressure of the fluid within the ventricle of the brain;

adjusting a temperature of the fluid within the ventricle of the brain based upon the measured pressure; and returning the fluid to the ventricle of the brain via the lumen defined by the probe.

* * * * *